US006413757B1

United States Patent
Cook et al.

(10) Patent No.: US 6,413,757 B1
(45) Date of Patent: Jul. 2, 2002

(54) 25312, A NOVEL HUMAN AGMATINASE-LIKE HOMOLOG

(75) Inventors: William James Cook, Natick; Rory A. J. Curtis, Southborough; Frank Spaltmann, Cambridge, all of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/514,521

(22) Filed: Feb. 28, 2000

(51) Int. Cl.[7] .............................. C12N 9/14; C12N 9/62; C12P 21/06; C07H 21/04
(52) U.S. Cl. ...................... 435/195; 435/69.1; 435/325; 536/23.2; 536/24.31
(58) Field of Search .................................. 435/195, 325, 435/69.1, 70.1; 536/23.2, 25.5, 24.31

(56) References Cited

U.S. PATENT DOCUMENTS 5,912,159 A * 6/1999 Vockley et al. ............. 435/227

FOREIGN PATENT DOCUMENTS

| EP | 0679716 A1 | 11/1995 |
|---|---|---|
| WO | 01/02568 A1 | 1/2001 |

OTHER PUBLICATIONS

Satishchandran, C. and Boyle, Stephen M., Purification and Properties of Agmatine Ureohydrolyase, A Putrescine Biosynthetic Enzyme in *Escherichia coli*, *Journal of Bacteriology*, Mar. 1986, pp. 843–848, vol. 165 (4), American Society for Microbiology.

Mistry, et al., "Cloning and Tissue–Specific Expression of Mammalian Agmatinase: A Potential Regulator of Agmatine Effects on Glomerular Filtration and Cell Proliferation in Renal Inflammation," Abstract No. A1938, *Journal of the American Society of Nephrology*, 1999, p. 384A, Program and Abstract Issue, 32nd Annual Meeting of the American Society of Nephrology; Miami Beach, Florida USA.

* cited by examiner

*Primary Examiner*—Nashaat T. Nashed
*Assistant Examiner*—Malgorzata A. Walicka
(74) *Attorney, Agent, or Firm*—Alston & Bird LLP

(57) ABSTRACT

The present invention relates to a newly identified human agmatinase-like arginase, designated "25312". The invention also relates to polynucleotides encoding the agmatinase-like arginase. The invention further relates to methods using the agmatinase-like polypeptides and polynucleotides as a target for diagnosis and treatment in disorders mediated by or related to the agmatinase-like arginase. The invention further relates to drug-screening methods using the polypeptides and polynucleotides to identify agonists and antagonists for diagnosis and treatment. The invention further encompasses agonists and antagonists based on the polypeptides and polynucleotides. The invention further relates to agonists and antagonists identified by drug screening methods with the polypeptides and polynucleotides as a target.

9 Claims, 7 Drawing Sheets

Input file Fbh25312b.seq; Output File 25312.trans
Sequence length 1700

```
TACTATAGGGAGTCGACCCACGCGTCCGCGGGTTCCGGCTCTGGCGCGTGCACACTCGCCTCGCCGTTCGGGACCAGCC

M   L   R   L   L          5
AGATCGCGGCGGCCTCGCGGGCGGTYTGGTCGGTGAGGTCTTGGCCGCGCGCGGCA ATG CTG AGG CTG CTG         15

A   S   G   C   A   R   G   P   G   P   G   V   G   A   R   P   A   A   G   L       25
GCG TCC GGG TGC GCC CGG GGC CCG GGG CCC GGC GTG GGC GCG CGT CCT GCC GCA GGG CTC       75

F   H   P   G   R   R   Q   S   R   Q   A   S   D   A   P   R   N   Q   P   P       45
TTT CAT CCG GGG CGC CGC CAG AGC CGC CAG GCT TCC GAC GCG CCC CGG AAC CAG CCC CCC      135

S   P   E   F   V   A   R   P   V   G   V   C   S   M   M   R   L   P   V   Q       65
AGC CCC GAG TTC GTG GCC CGG CCG GTG GGC GTC TGC TCC ATG ATG CGC CTG CCG GTG CAG      195

T   S   P   E   G   L   D   A   A   F   I   G   V   P   L   D   T   G   T   S       85
ACC TCC CCC GAG GGG CTG GAC GCT GCC TTC ATC GGG GTG CCC CTG GAT ACT GGG ACC TCC      255

N   R   P   G   A   R   F   G   P   R   R   I   R   E   E   S   V   M   L   R      105
AAC CGG CCT GGG GCG AGA TTC GGA CCT CGC CGC ATC CGG GAA GAA TCA GTG ATG CTT CGG      315

T   V   N   P   S   T   G   A   L   P   F   Q   S   L   M   V   A   D   L   G      125
ACA GTC AAT CCT AGC ACG GGG GCC CTC CCC TTC CAG TCC CTC ATG GTT GCA GAC CTA GGC      375

D   V   N   V   N   L   Y   N   L   Q   D   S   C   R   Q   I   Q   E   A   Y      145
GAT GTG AAT GTC AAT CTT TAC AAC CTT CAG GAC AGC TGC CGG CAA ATT CAA GAG GCC TAT      435

E   K   I   V   A   A   G   C   I   P   L   T   L   G   G   D   H   T   I   T      165
GAG AAA ATT GTA GCA GCT GGC TGT ATT CCT CTG ACC TTG GGT GGA GAT CAC ACA ATC ACA      495

Y   P   I   L   Q   A   M   A   K   K   H   G   P   V   G   L   L   H   V   D      185
TAT CCC ATA TTG CAA GCG ATG GCA AAA AAG CAT GGC CCA GTG GGG CTG CTG CAC GTG GAT      555

A   H   T   D   T   T   D   K   A   L   G   E   K   L   Y   H   G   A   P   F      205
GCG CAC ACG GAC ACG ACC GAC AAG GCC CTA GGA GAG AAG CTC TAC CAC GGG GCG CCC TTC      615

R   R   C   V   D   E   G   L   L   D   C   K   R   V   V   Q   I   G   I   R      225
CGC CGG TGT GTG GAT GAG GGT CTC CTG GAC TGT AAG CGT GTG GTG CAG ATT GGC ATC CGG      675

G   S   S   T   T   L   D   P   Y   R   Y   N   R   S   Q   G   F   R   V   V      245
GGC TCT TCC ACG ACC TTG GAT CCC TAC AGA TAC AAC CGG AGC CAG GGC TTC CGG GTA GTC      735

L   A   E   D   C   W   M   K   S   L   V   P   L   M   G   E   V   R   Q   Q      265
CTG GCT GAA GAC TGC TGG ATG AAG TCG CTG GTT CCT CTG ATG GGG GAA GTC AGG CAG CAG      795

M   G   G   K   P   I   Y   I   S   F   D   I   D   A   L   D   P   A   Y   A      285
ATG GGA GGC AAA CCC ATT TAT ATC AGC TTT GAT ATT GAC GCT CTG GAT CCT GCC TAT GCG      855

P   G   T   G   T   P   E   I   A   G   L   T   P   S   Q   A   L   E   I   I      305
CCA GGG ACA GGG ACA CCT GAA ATT GCT GGT CTC ACT CCT AGT CAG GCT CTG GAG ATC ATC      915

R   G   C   Q   G   L   N   V   M   G   C   D   L   V   E   V   S   P   P   Y      325
AGG GGT TGT CAA GGC CTG AAC GTG ATG GGC TGT GAT CTT GTC GAA GTT TCA CCA CCG TAT      975

D   L   S   G   N   T   A   L   L   A   A   N   L   L   F   E   M   L   C   A      345
GAT CTT TCT GGG AAC ACA GCC CTG CTG GCG GCT AAC CTG CTG TTT GAG ATG CTA TGT GCT     1035

L   P   K   V   T   T   V   *                                                       353
CTC CCC AAA GTG ACA ACC GTC TGA                                                     1059
```

FIG. 1.

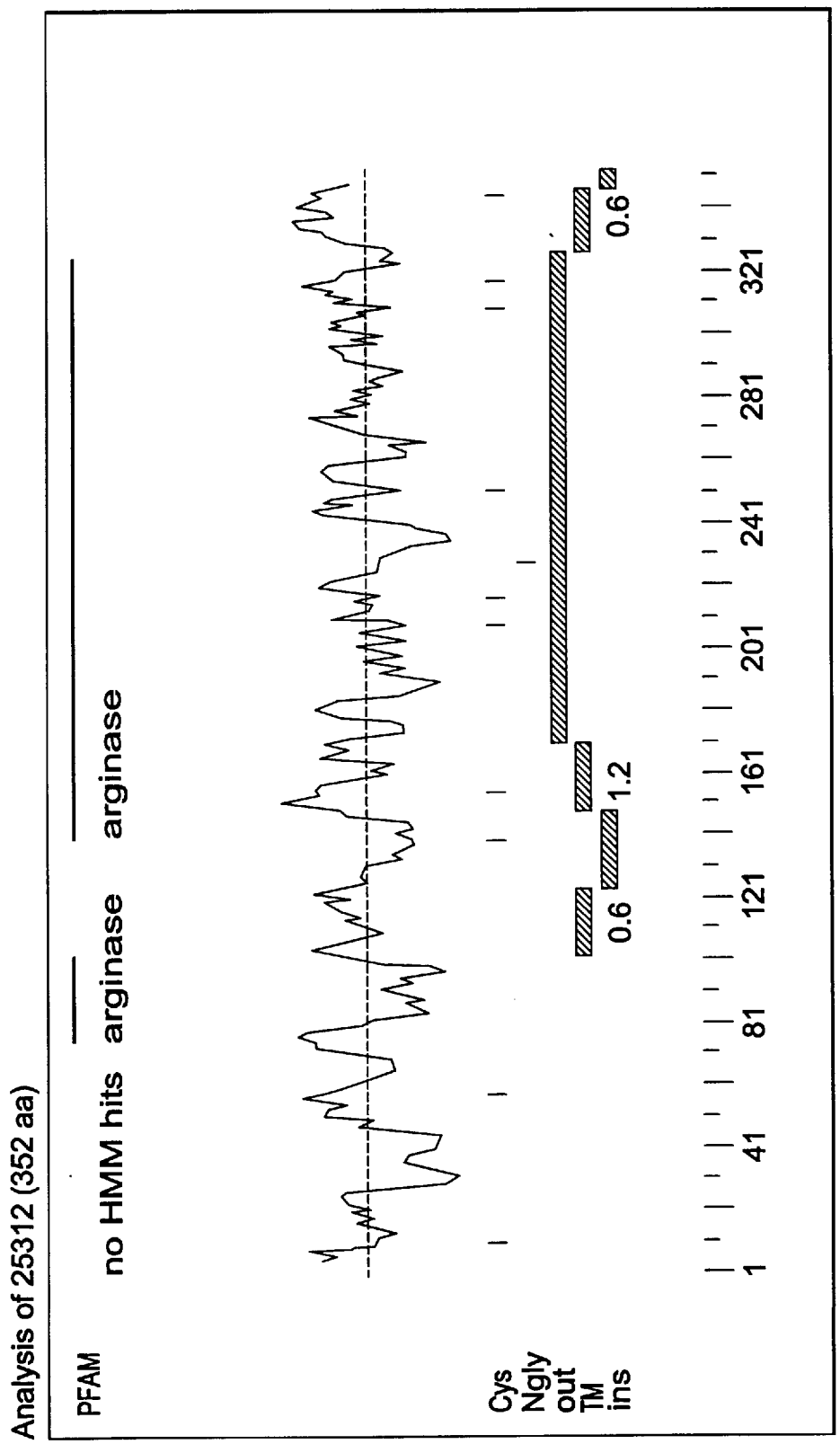

Prosite Pattern Matches for 25312

>PS00001/PDOC00001/ASN_GLYCOSYLATION N-glycosylation site.

Query: 237    NRSQ    240

>PS00004/PDOC00004/CAMP_PHOSPHO_SITE cAMP_ and cGMP-dependent protein kinase phosphorylation site.

Query: 30    RRQS    33

>PS00005/PDOC00005/PKC_PHOSPHO_SITE Protein kinase C phosphorylation site.

Query: 85    SNR    87
Query: 137   SCR    139
Query: 191   TDK    193

>PS00006/PDOC00006/CK2_PHOSPHO_SITE Casein kinase II phosphorylation site.

Query: 66    TSPE    69
Query: 229   TTLD    232

>PS00007/PDOC00007/TYR_PHOSPHO_SITE Tyrosine kinase phosphorylation site.

Query: 193    KALGEKLY    200

>PS00008/PDOC00008/MYRISTYL N-myristoylation site.

Query: 18     GARPAA    23
Query: 70     GLDAAF    75
Query: 159    GGDHTI    164
Query: 212    GLLDCK    217
Query: 223    GIRGSS    228
Query: 295    GLTPSQ    300

>PS00009/PDOC00009/AMIDATION Amidation site.

Query: 28    PGRR    31

>PS00147/PDOC00135/ARGINASE_1 Arginase and agmatinase signature 1.

Query: 158    LGGDHTIT    165

FIG. 4.

25312, A NOVEL HUMAN AGMATINASE-LIKE HOMOLOG

FIELD OF THE INVENTION

The present invention relates to a newly identified human agmatinase-like arginase, designated "25312". The invention also relates to polynucleotides encoding the agmatinase-like arginase. The invention further relates to methods using the agmatinase-like polypeptides and polynucleotides as a target for diagnosis and treatment in disorders mediated by or related to the agmatinase-like arginase. The invention further relates to drug-screening methods using the polypeptides and polynucleotides to identify agonists and antagonists for diagnosis and treatment. The invention further encompasses agonists and antagonists based on the polypeptides and polynucleotides. The invention further relates to agonists and antagonists identified by drug screening methods with the polypeptides and polynucleotides as a target.

BACKGROUND OF THE INVENTION

Human agmatinase is an enzyme that plays a role in the hydrolysis of agmatine [4-(aminobutyl)guanidine] to putrescine and other polyamines such as spermine and spermidine which are essential for DNA replication, cell homeostasis and cell transformation. Polyamines are required for entry and progression of the cell cycle. Also, augmentation of polyamine levels is essential for cellular transformation. Agmatine is a metabolite of arginine via arginine decarboxylase (ADC) and is implicated in the attenuation of cellular polyamine levels (Satriano et al. (1998) *J. Biol. Chem.* 273 (25):15313–15316). Agmatine represents an alternate pathway to polyamine production in contradistinction to the well-studied pathway mediated by omithine decarboxylase (ODC) which acts in the metabolism of arginine to yield putrescine which feeds into polyamine synthesis. End-products of arginine metabolism include the cell-signaling molecules: NO, glutamate, and agmatine. (Wu et al., (1998) *Biochem. J* 336:1–17). Mammalian ADC is membrane associated and expressed in the inner membranes of mitochondria.

Agmatine is widely and unevenly distributed in a variety of mammalian tissues including serum. The tissues where agmatine has been identified include: stomach, aorta, small intestine, large intestine, spleen, lung, vas deferens, adrenal gland, kidney, heart, liver, skeletal muscle, testes, and brain. The highest concentration was found in stomach, aorta, and small intestine (Raasch, W. et al., (1995) *Life Sciences* 56 pp. 2319–2330). Agmatine binds to $\alpha_2$-adrenergic and imidazoline receptors and is bioactive in a number of tissues (Wu et al., (1998) *Biochem. J* 336:1–17). It is contained in neurons and is found in serum which is consistent with its role as a putative neurotransmitter and/or a hormone. Agmatine potentiates the analgesic effects of morphine and clonidine in a dose-dependent manner and decreases the $EC_{50}$ of morphine and clonidine by more than 75% in a mouse tail-flick test. Intrathecal agmatine at high doses causes a decrease in the pain threshold (Jin, Li et al., (1999) *Acta Phannacologica Sinica* 20 (1): 81–85). The enzyme has been isolated from rat brain and was localized primarily in the mitochondria wherein it degrades the substrate, agmatine at its site of action (Regunathan et al.,(1996) *J. Neurochem.* 67(4):1761–65). Specifically, the enzyme is localized in the mitochondrial matrix.

It is presumed that agmatine is a biologically active molecule with numerous physiological roles including, but not limited to: binding to $\alpha_2$-adrenergic and imidazoline receptors, causing release of catecholamine from adrenal chromaffin cells, stimulating release of insulin and uptake of Ca in pancreatic cells, inhibitor of lipolysis in rat adipocytes, increase glucose uptake and glycogen content of the rat diaphragm, and increase glucose oxidation and lipogenesis in fat pads and glucose oxidation in isolated fat cells (Raasch, W. et al., (1995) *Life Sciences* 56 pp. 2319–2330).

The concentration of agmatine in the whole brain is comparable to that of other neurotranstritters. It is unevenly distributed with the highest concentration in the hypothalamus, forebrain, and cerebral cortex (Reis et al. (1999) *Annals of the NY Academy of Sciences* 881: 65–80). Agmatine is synthesized and stored in astrocytes (Youngson et al., *Ann. NY Acad. Sci.* 763: 440–444).

Agmatinase (agmatine ureohydrolase) is an enzyme that hydrolyzes agmatine to form putrescine and urea. Putrescine along with spermine and spermidine are polyamines.

Polyamines such as putrescine, spermidine, and spermine are required for DNA replication, proliferation, and cell homeostasis. Omithine decarboxylase (ODC) is the first rate-limiting enzyme of polyamine biosynthesis and one of the most highly regulated eukaryotic enzymes. Cellular polyamine transporters are stimulated by many of the same factors that induce ODC activity. Cellular polyamine uptake occurs both in normal and rapidly proliferating cells and tumor lines (Moulinoux et al. (1991) *Cell. Mol. Biol.* 37:773–783; Bogle et al. (1994) *Am. J. Physiol.* 266:C776–C783; Holley et al. (1992) *Cancer Res.* 52:4190–4195).

Polyamines have been reported in the herpes simplex virion (HSV) (Gibson et al. (1973) *Polyamines in Normal and Neoplastic Growth,* edited by D. H. Russell, Raven Press, N.Y.). The polyamines may serve as specific structural components of the virion and serve to neutralize the electronegativity of DNA. Agmatinase may play a role in HSV infection as it is induced during the latent phase of HSV replication (unpublished data). Also, 25312 expression is induced during infection by the DNA virus HBV (unpublished data). Thus, high levels of polyamine synthesis via the agmatinase pathway may be a requirement for DNA viruses.

Intracellular polyamine concentrations are autoregulated by the induction of the protein antizyme (Matsufaji et al. (1995) *Cell* 80:51–60). Antizyme binds to ODC and inhibits its activity and accelerates its degradation (Hayashi et al. (1996) *Trends Biochem Sci.* 21:27–30). More recently, antizyme has been shown to suppress polyamine transporters (Mitchell et al. (1994) *Biochem. J.* 299:19–22; Suzuki (1994) *Proc. Natl. Acad. Sci.* 91:8930–8934). Thus, antizyme through its ability to suppress both the polyamine biosynthetic enzyme ODC and polyamine transporters is an effective endogenous mechanism for limiting intracellular polyamine levels.

Recent research has demonstrated the induction of antizyme by agmatine. The induced antizyme can bind to omithine decarboxylase (ODC) and depress polyamine biosynthesis and transport. (Satriano et al. (1998) *J. Biol. Chem.* 273: 15313–15316). The capacity of agmatine to induce antizyme is demonstrated by (a) an agmatine-dependent translational frameshift of antizyme mRNA to produce a full-length protein and (b) suppression of agmatine-dependent inhibitory activity by either anti-antizyme IgG or antizyme inhibitor (Satriano et al. (1998) *J. Biol. Chem.* 273 (25):15313–15316).

There is evidence that agmatine has several potential roles in mammalian physiology, including: acting as a neurotransmitter, as a secretogogue and as an endogenous inhibitor of all isoforms of NOS, and it may play a role in modulating the state of macrophage activation during inflammation by regulating NOS activity and NO production (Sastre et al. (1998) *Biochem. J.* 330:1405–1409).

Agmatine (AGM) has long been characterized as a constituent of bacteria, plants and some invertebrates (Tabor and Tabor (1984) *Ann. Rev. Biochem.* 53:749–790). More recently, agmatine was shown to be expressed in rat brain (Li, G. et al. (1994) *Science* 263:966–969). Agamatine is an endogenous ligand at imidazoline and α-adrenergic receptors to which it binds with high affinity (Tabor et al. (1984) *Ann. Rev. Biochem.* 53:749–790). Agmatine also has properties of an endogenous neurotransmitter. However, its actual role in normal brain function has not yet been established (Reis et al. (1998) *Adv Pharmacol* 42:645–9). Agmatine is locally synthesized in the brain and stored in a large number of neurons with selective distribution in the central nervous system. Also, it can be enzymatically degraded by agmatinase in the synaptosomes (Reis et al., (1999) *Annals of the NY Academy of Sciences* 881:65–80.)

Agmatine which is an endogenous ligand of imidazoline receptors is biologically active in the nervous system and many other tissues in mammals (Li et al., (1994) *Science*, 263:966–969).

Agmatine stimulates the release of catecholamines from adrenal chromaffin cells, increases arterial blood pressure when injected into rats, stimulates the release of insulin from β-cells in pancreatic islets, and increases the release of gonadorelin from the hypothalamus (Galea et al., (1996) *Biochem. J.* 316:247–249). Also, it potentiates opioid analgesia and prevents the tolerance induced by opioids (Kolesnikov et al., (1996) *Eur. J. Pharmacol.* 296:17–22). Agmatine has analgesic effects and potentiates morphine and clonidine analgesia by activation of imidazoline receptors, but cannot prolong the analgesic time of morphine (Li, et al., (1999) *Acta Pharmalogica Sinica* 20(1):81–85). Therefore, regulation of agmatine degradation may be useful in the treatment of pain.

Agmatine is an antimitogen capable of inhibiting the proliferation of vascular muscle cells (Reis et al., (1999) *Annals of the NY Academy of Sciences* 881:65–80.)

Agamatine has been shown to play a role in modulating the state of macrophage activation during inflammation (Sastre et al., (1998) *Biochem. J.* 330:1405–1409). Sastre et al. demonstrated that macrophages express the enzymes ADC and agmatinase and that the enzyme activities are regulated during inflammation. ADC and agmatinase are constituitively expressed in macrophages and that lipopolysaccharides (LPS) dose-dependently and reversibly modulated the basal and evoked activity of both enzymes as well as initiating induction of iNOS indicating that the enzymes are regulated. Agmatine is an inhibitor of all isoforms of nitric oxide synthases (NOS) (Reis et al. (1999) *Annals of NY Academy of Science* 881: 65–80).

Agmatine can play a role in the etiology of viral infections, specifically Herpes Simplex Virus (HSV) as relates to the formation of polyamines in the virus (Gibson and Roizman, (1973) *Polyamines in Normal and Neoplastic Growth*. ed. Russell, Raven Press, N.Y.). The polyamines, which can be produced due to the action of agmatinase on agmatine, can act as specific structural components of the virion. It was demonstrated that highly purified preparations of enveloped HSV contain the polyamines spermidine and spermine in a nearly constant molar ratio of 1.6±0.2 (Gibson and Roizman (1971) *Proc. Nat. Acad. Sci. U.S.A.* 68:2818–2821). Thus, the polyamines could serve to neutralize the electronegativity of the DNA.

The polyamines have been compartmentalized to the nucleocapsid in the HSV. Moreover, there is a segregation of the spermine and spermidine in the HSV with spermine inside the nucleus and spermidine outside (Gibson and Roizman (1971) *Proc. Nat. Acad. Sci. USA* 68: 2818–2821).

It has been observed that agmatinase activity is expressed with regional variability in the rat. The highest levels were observed in the hypothalamus, moderate expression in the medulla oblongata and hippocampus and lowest levels in the striatum and cerebral cortex (Sastre et al. (1996) *J. Neurochem.* 67: 1761–65).

Carvajal et al. (1999) *Biochem. Biophys. Res. Comm.* 264:196–200 dislcoses a coupled urease system that can be used to assay agmatinase activity and binding. Agmatinase activity can also be assayed using a two-step procedure in which [guanido-$^{14}$C] agmatine is first hydrolyzed to [$^{14}$C] urea and putrescine and then [$^{14}$C] urea is hydrolyzed by added urease to $^{14}CO_2$ and $NH_3$. This method has been widely used to assay bacterial agmatinases (Satishchandran C. et al. (1986) *J. Bacteriol.* 165:843–848). This method can be adapted for use in mammalian tissues (Sastre, M. et al. (1996) *J. Neurochem.* 67: 1761–65). It has been determined that the agmatinase isolated from rat brain has maximal activity a pH 8–8.5 and an apparent $K_m$ of 5.3±0.99 mM. There are some known inhibitors of agmatinase including the divalent cation $Mn^{+2}$ (Sastre et al., (1996) *J. Neurochem* 67: 1761–1765) and other organic inhibitors including N-isoamylene agmatine (Khramov. V. (1976) *Vopr Med Khim* 22(6): 804–808). and the organic inactivator diethyl pyrocarbonate (DEPC) (Carvajal, N. et al. (1999) *Biochem. Biophys. Res. Commun.* 264 (1):196–200).

Mechanistic studies have been performed with agmatinases isolated from bacteria such as *E. coli* to ascertain the critical sites in the native protein for catalytic function and substrate binding (Carvajal (1999) *Biochem. Biophys. Res. Commun.* 264(1):196–200). Additionally, various inhibitors have been identified which affect agmatinase activity, including N-isoamylene agmatine (Kharamov (1976) *Vopr Med Khim* 1976 22 (6):804–808). Additionally, ornithine and arginine have been shown to be inhibitors of agmatinase. Ornithine inhibited agmatinase in *E.coli* noncompetitively while it inhibited arginine competitively (Satischandran, C. et al. (1986) *J. Bacteriol.* 165: 843–848). EDTA and EGTA were shown to be irreversible inactivators of agmatinase. In the bacterium, *E.coli*, studies indicated that agmatinase requires a metal for its structural stability rather than its catalytic activity, and that its production is induced by agmatine and that it serves a role in the production of the polyamine putrescine and that it is not a major source of carbon and energy (Satischandran, C. et al. (1986) *J. Bacteriol.* 165: 843–848).

The reaction catalyzed by agmatinase is similar to that catalyzed by arginase (EC 3.5.3.1) which hydrolyzes arginine to ornithine and urea. However, in rat brain differences have been noted. Arginase activity localized primarily in the soluble and cystolic fractions, whereas agmatinase localized primarily in the mitochondria. (Sastre, et al. (1996) *J. Neurochem.* 67: 1761–1765).

Thus, agmatine, as a potential metabolic precursor for polyamines, plays a key role in cellular physiology and cell homeostasis. It can have several important biochemical effects ranging from but not limited to effects on the central nervous system, the cardiovascular system, inflammation, pain analgesia, cell proliferation in cancer, and viral replication.

Accordingly, agmatinases are a major target for drug action and development. Thus, it is valuable to the field of pharmaceutical development to identify and characterize novel agmatinases and tissues and disorders in which agmatinases are differentially expressed. The present invention advances the state of the art by providing a novel human agmatinase and tissues and disorders in which expression of a human agmatinase is relevant. Accordingly, the invention provides methods directed to expression of the agmatinase.

SUMMARY OF THE INVENTION

It is an object of the invention to identify novel human agmatinases and tissues and disorders in which expression of the agmatinase is relevant.

It is a further object of the invention to provide novel human agmatinase polypeptides that are useful as reagents or targets in agmatinase assays applicable to treatment and diagnosis of disorders mediated by or related to the agmatinase.

It is a further object of the invention to provide polynucleotides corresponding to the agmatinase polypeptides that are useful as targets or reagents in agmatinase assays applicable to treatment and diagnosis mediated by or related to the agmatinase and useful for producing novel agmatinase polypeptides by recombinant methods. A specific object of the invention is to identify compounds that act as agonists and antagonists and modulate expression of agmatinase in specific tissues and disorders.

The invention is thus based on the identification and expression of a human agmatinase-like protein that is a member of the arginase family, especially in specific tissues and disorders. The protein of the invention, i.e., 25312, is referred to herein as an "agmatinase." "Agmatinase," when referring to the protein of the invention, is intended to refer to the sequences shown in FIG. 1, which represent agmatinase-like nucleic acids or protein in the arginase family.

The invention provides methods of screening for compounds that modulate expression or activity of the agmatinase polypeptides or nucleic acid (DNA or RNA) in the specific tissues or disorders.

The invention also provides a process for modulating agmatinase polypeptide or nucleic acid expression or activity, especially using the screened compounds.

Modulation may be used to treat conditions related to aberrant activity or expression of the agmatinase polypeptides or nucleic acids. The invention also provides assays for determining the activity of or the presence or absence of the agmatinase polypeptides or nucleic acid molecules in specific biological samples, including for disease diagnosis.

The invention also provides assays for determining the presence of a mutation in the polypeptides or nucleic acid molecules, including for disease diagnosis.

The invention provides isolated agriatinase polypeptides, including a polypeptide having the amino acid sequence shown in SEQ ID NO:1 or the amino acid sequence encoded by the cDNA deposited as ATCC Patent Deposit No. PTA-1844 on May 9, 2000 ("the deposited cDNA").

The invention also provides an isolated agmatinase nucleic acid molecule having the sequence shown in SEQ ID NO:2 or encoded by the deposited cDNA.

The invention also provides variant polypeptides having an amino acid sequence that is substantially homologous to the amino acid sequence shown in SEQ ID NO:1 or encoded by the deposited cDNA.

The invention also provides variant nucleic acid sequences that are substantially homologous to the nucleic acid sequence shown in SEQ ID NO:2 or in the deposited cDNA.

The invention also provides fragments of the polypeptide shown in SEQ ID NO:1 and nucleotide sequence shown in SEQ ID NO:2, as well as substantially homologous to the fragments of the polypeptide or nucleic acid.

The invention further provides nucleic acid constructs comprising the nucleic acid molecules described herein. In a preferred embodiment, the nucleic acid molecules of the invention are operatively linked to a regulatory sequence.

The invention also provides vectors and host cells that express the agmatinase and provides methods for expressing the agmatinase nucleic acid molecules and polypeptides in specific cell types and disorders, and particularly recombinant vectors and host cells.

The invention also provides methods of making the vectors and host cells and provides methods for using them to produce agmatinase nucleic acid molecules and polypeptides and to assay expression and cellular effects of expression of the agmatinase nucleic acid molecules and polypeptides in specific cell types and disorders.

The invention also provides antibodies or antigen-binding fragments thereof that selectively bind the agmatinase polypeptides and fragments.

In still a further embodiment, the invention provides a computer readable means containing the nucleotide and/or amino acid sequences of the nucleic acids and polypeptides of the invention.

BRIEF DESCRIPTION OF THE DRAWINGS

FIG. 1 shows the agmatinase nucleotide sequence (SEQ ID NO:2) and the corresponding amino acid sequence (SEQ ID NO:1).

FIG. 3 shows a hydrophobicity plot of the agmatinase.

FIG. 4 shows an analysis of the agmatinase open reading frame for amino acids corresponding to the specific functional sites.

DETAILED DESCRIPTION OF THE INVENTION

Figure 2:
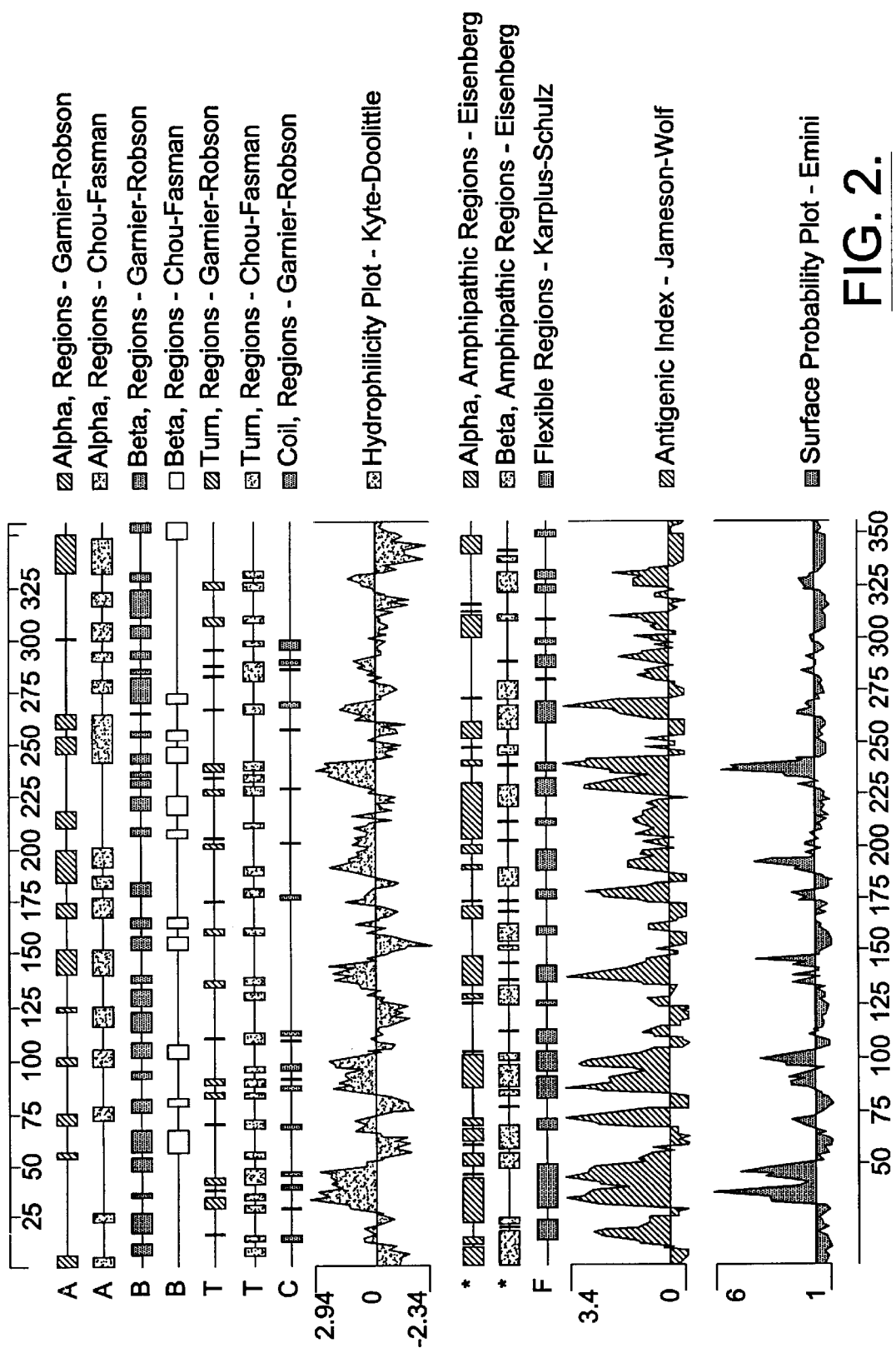
FIG. 2 shows an analysis of the agmatinase amino acid sequence: αβturn and coil regions; hydrophilicity; amphipathic regions; flexible regions; antigenic index; and surface probability plot.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meanings as commonly understood by one of ordinary skill in the art to which this invention belongs. Although any methods and materials similar or equivalent to those described herein can be used in the practice or testing of the invention, the preferred methods and materials are now described. All publications mentioned herein are incorporated by reference for the purpose of describing and disclosing cell lines, vectors, and methodologies which are reported in the publications which might be used in connection with the invention. Nothing is to be construed as an admission that the invention is not entitled to antedate such disclosure by virtue of prior invention.

The invention is thus based on the identification and expression of a human agmatinase-like protein that is a member of the arginase family, especially in specific tissues and disorders. The protein of the invention, i.e., 25312, is referred to herein as an "agmatinase." "Agmatinase," when referring to the protein of the invention, is intended to refer to the sequences shown in FIG. 1, which represent agmatinase-like nucleic acids or protein in the arginase family.

"Nucleic acid sequence" as used herein, refers to an oligonucleotide, nucleotide, or polynucleotide, and fragments and portions thereof, and to DNA or RNA of genomic or synthetic origin which may be single-or double-stranded, and represents the sense or antisense strand. Similarly, "amino acid sequence" as used herein refers to an oligopeptide, peptide, polypeptide, or protein sequence, and fragments or portions thereof, and to naturally occurring, recombinant or synthetic molecules.

Where "amino acid sequence" is recited herein to refer to an amino acid sequence of a naturally occurring protein molecule, amino acid sequence and like terms, such as "polypeptide" or "protein" are not meant to limit the amino acid sequence to the complete, native amino acid sequence associated with the recited protein.

Agmatinase as used herein, refers to the amino acid sequences of substantially purified agmatinase obtained from any species, particularly mammalian, including bovine, ovine, porcine, murine, equine, and preferably human, from any source whether natural, synthetic, semi-synthetic, or recombinant.

A "deletion" as used herein, refers to a change in either amino acid or nucleotide sequence in which one or more amino acids or nucleotide residues, are absent.

An "insertion" or "addition", as used herein, refers to a change in an amino acid or nucleotide sequence resulting in the addition of one or more amino acid or nucleotide residues.

A "substitution" as used herein, refers to the replacement of one or more amino acids or nucleotides by different amino acids or nucleotides, respectively.

The term "biologically active" as used herein, refers to a protein having structural, regulatory, or biochemical functions of the agmatinase. Also "immunologically" active refers to the capability of the natural, recombinant, or synthetic agmatinase, or any oligopeptide thereof, to induce a specific immune response in appropriate animals or cells and to bind with specific antibodies.

The term "agonist" as used herein, refers to a molecule which, when bound to agmatinase causes a change in agmatinase which modulates activity of agmatinase. Agonists may include proteins, nucleic acids, carbohydrates or any other molecules.

The terms "antagonist" or "inhibitor", as used herein, refers to a molecule which blocks or modulates the biological activity of agmatinase. Antagonists may include proteins, nucleic acids, carbohydrates, or any other molecules.

The term "modulate" as used herein, refers to a change in the biological level or activity of agmatinase. Modulation may be an increase or a decrease in protein activity, a change in binding characteristics of agmatinase to its substrate or effector molecule, or any other change in the biological, functional, or immunological properties of agmatinase.

The term "derivative" as used herein, refers to the chemical modifications of a nucleic acid encoding agmatinase or the encoded agmatinase. Illustrations of such modifications would be replacement of hydrogen by an alkyl, acyl, or amino group. A nucleic acid derivative would encode a polypeptide which retains essential biological characteristics of the natural molecule.

Polypeptides

The invention is based on the identification of a novel human agmatinase and the polynucleotides encoding the agmatinase.

The invention relates to a novel human agmatinase having the amino acid sequence as shown in FIG. 1 (SEQ ID NO:1) or having the amino acid sequence encoded by the deposited cDNA, ATCC Patent Deposit No. PTA-1844.

The deposit will be maintained under the terms of the Budapest Treaty on the International Recognition of the Deposit of Microorganisms. The deposit is provided as a convenience to those of skill in the art and is not an admission that a deposit is required under 35 USC §112. The deposited sequence, as well as the polypeptide encoded by the sequence, is incorporated herein by reference and controls in the event of any conflict, such as sequencing error, with description in this application. "Agmatinase polypeptide" or "agmatinase protein" refers to the polypeptide in SEQ ID NO:1 or encoded by the deposited cDNA. The term "agmatinase polypeptide" or "agmatinase protein" further includes the numerous variants described herein, as well as fragments derived from the full-length agmatinase and variants.

The agmatinase cDNA was identified in a human cDNA library. Specifically, an expressed sequence tag (EST) found in a human primary osteoblast library was selected based on homology to a known family of arginase sequences. Positive clones were sequenced and the overlapping fragments were assembled. The agmatinase amino acid sequence is shown in FIG. 1 and SEQ ID NO:1. The agmatinase cDNA sequence is shown in FIG. 1 and SEQ ID NO:2.

Figure 5:
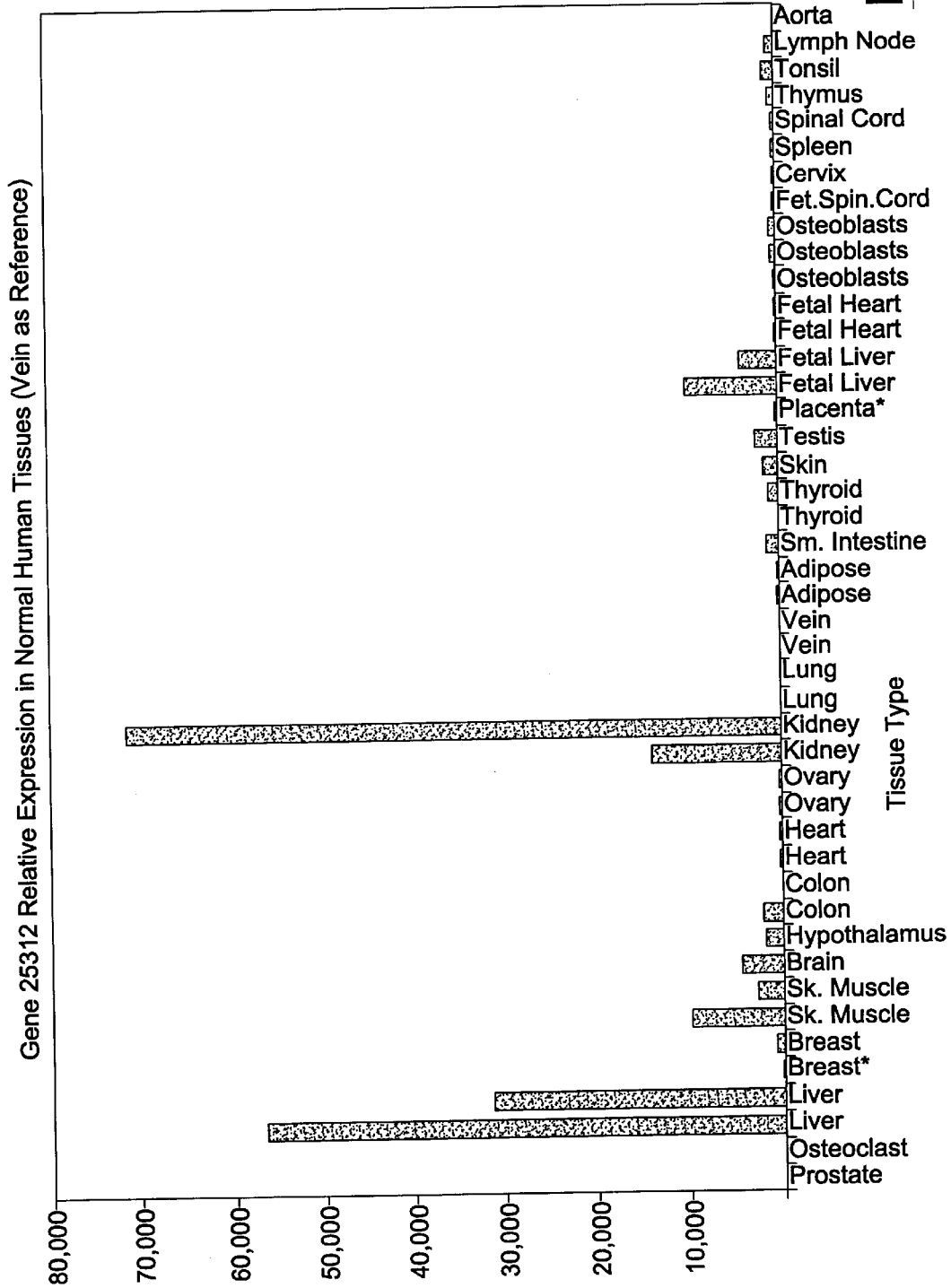
FIG. 5 shows expression of the 25312 agmatinase in various normal human tissues using Taqman(quantitative reverse transcriptase-PCR). The value for 25312 mRNA expression in the vein sample was made equal to one. Values obtained for all other tissues were made relative to that for vein.

In one preferred embodiment, the agmatinase polypeptide is expressed in the following mammalian tissues: liver, brain, colon, vein, kidney, skeletal muscle, esophagus, hypothalamus, small intestine, thyroid, thymus, tonsil, lymph node, prostrate, testes, and skin. Expression was highest in liver, kidney and skeletal muscle tissue (FIG. 5).

The present invention thus provides an isolated or purified agmatinase and variants and fragments thereof.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified".

The agmatinase can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

An agmatinase polypeptide is also considered to be isolated when it is part of a membrane preparation or is purified and then reconstituted with membrane vesicles or liposomes.

The language "substantially free of chemical precursors or other chemicals" includes preparations of the agmatinase polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the agmatinase polypeptide comprises the amino acid sequence shown in SEQ ID NO:1. However, the invention also encompasses sequence variants. Variants include a substantially homologous protein encoded by the same genetic locus in an organism, i.e., an allelic variant.

Variants also encompass proteins derived from other genetic loci in an organism, but having substantial homology to the agmatinase of SEQ ID NO:1. Variants also include proteins substantially homologous to the agmatinase but derived from another organism, i.e., an ortholog. Variants also include proteins that are substantially homologous to the agmatinase that are produced by chemical synthesis. Variants also include proteins that are substantially homologous to the agmatinase that are produced by recombinant methods. It is understood, however, that variants exclude any amino acid sequences disclosed prior to the invention.

As used herein, two proteins (or a region of the proteins) are substantially homologous when the amino acid sequences are at least about 70–75%, 75–80%, typically at least about 80–85%, 85–90%, and most typically at least about 90–95% or more homologous. A substantially homologous amino acid sequence, according to the present invention, will be encoded by a nucleic acid sequence hybridizing to the nucleic acid sequence, or portion thereof, of the sequence shown in SEQ ID NO:2 under stringent conditions as more fully described below.

To determine the percent identity of two amino acid sequences or of two nucleic acid sequences, the sequences are aligned for optimal comparison purposes e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequences herein having 352 amino acid residues, at least 106, preferably at least 141, more preferably at least 176, even more preferably at least 211, and even more preferably at least 246, 282, and 317 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the agmatinase. Similarity is determined by conserved amino acid substitutions. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

TABLE 1.

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991).

A preferred, non-limiting example of such a mathematical algorithm is described in Karlin et al. (1993) *Proc. Natl. Acad. Sci. USA* 90:5873–5877. Such an algorithm is incorporated into the NBLAST and XBLAST programs (version 2.0) as described in Altschul et al. (1997) *Nucleic Acids Res.* 25:3389–3402. When utilizing BLAST and Gapped BLAST programs, the default parameters of the respective programs (e.g., NBLAST) can be used. See http://www.ncbi.nlm.nih.gov. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444–453) algorithm which has been incorporated into the GAP program in the GCG software package (available at http://www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res.* 12(1):387) (available at http://www.gcg.com), using a NWSgap-dna.CMP matrix and a gap weight of 40, 50,60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM 120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3–5; and FASTA described in Pearson et al. (1988) *PNAS* 85:2444–8.

A variant polypeptide can differ in amino acid sequence by one or more substitutions, deletions, insertions, inversions, fusions, and truncations or a combination of any of these. Variant polypeptides can be fully functional or can lack function in one or more activities, including but not limited to those functions/activities disclosed in the background herein.

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the agmatinase polypeptide. This includes preventing immunogenicity from pharmaceutical formulations by preventing protein aggregation.

Amino acids that are essential for function can be identified by methods known in the art, such as site-directed mutagenesis or alanine-scanning mutagenesis (Cunningham et al. (1985) *Science* 244:1081–1085). The latter procedure introduces single alanine mutations at every residue in the molecule. The resulting mutant molecules are then tested for agmatinase activity such as by measuring the formation of urea and putrescine (Sastre et al. (1996) *J. Neurochem.* Vol. 67, No. 4, 1762–1763). Sites that are critical for agmatinase can also be determined by structural analysis such as crystallization, nuclear magnetic resonance or photoaffinity labeling (Smith et al. (1992) *J. Mol. Biol.* 224:899–904; de Vos et al. (1992) *Science* 255:306–312).

Substantial homology can be to the entire nucleic acid or amino acid sequence or to fragments of the sequence.

The invention thus also includes polypeptide fragments of the agmatinase. Fragments can be derived from the amino acid sequence shown in SEQ ID NO:1. However, the invention also encompasses fragments of the variants of the agmatinases as described herein.

The fragments to which the invention pertains, however, are not to be construed as encompassing fragments that may be disclosed prior to the present invention.

Accordingly, a fragment can comprise at least about 5, 10, 15, 20, 25, 30, 35, 40, 45, 50 or more contiguous amino acids. Fragments can retain one or more of the biological activities of the protein, for example the ability to bind to or hydroxylate agmatine, as well as fragments that can be used as an immunogen to generate agmatinase antibodies.

Biologically active fragments (peptides which are, for example, 5, 10, 15, 20, 30, 35, 40, 50, 100 or more amino acids in length) can comprise a domain or motif, e.g., catalytic site, regulatory site, site important for effector or substrate recognition or binding, agmatinase signature, and sites for N-glycosylation, protein kinase C phosphorylation, casein kinase II phosphorylation, tyrosine kinase phosphorylation, cGMP-dependent protein kinase phosphorylaltion, N-myristoylation, and amidation. Further possible fragments include the catalytic site or domain binding sites for agmatine.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the agmatinase and variants. These epitope-bearing peptides are useful to raise antibodies that bind specifically to an agmatinase polypeptide or region or fragment. These peptides can contain at least 10, 12, at least 14, or between at least about 15 to about 30 amino acids.

Non-limiting examples of antigenic polypeptides that can be used to generate antibodies include but are not limited to peptides derived from an extracellular site. Regions having a high antigenicity index are shown in FIG. 2. However, intracellularly-made antibodies ("intrabodies") are also encompassed, which would recognize intracellular peptide regions.

The epitope-bearing agmatinase polypeptides may be produced by any conventional means (Houghten, R. A. (1985) *Proc. Natl. Acad. Sci. USA* 82:5131–5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the agmatinase fragment and an additional region fused to the carboxyl terminus of the fragment.

The invention thus provides chimeric or fusion proteins. These comprise an agmatinase peptide sequence operatively linked to a heterologous peptide having an amino acid sequence not substantially homologous to the agmatinase. "Operatively linked" indicates that the agmatinase peptide and the heterologous peptide are fused in-frame. The heterologous peptide can be fused to the N-terminus or C-terninus of the agmatinase or can be internally located.

In one embodiment the fusion protein does not affect agmatinase function per se. For example, the fusion protein can be a GST-fusion protein in which the agmatinase sequences are fused to the N- or C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant agmatinase. In certain host cells (e.g., mammalian host cells), expression and/or secretion of a protein can be increased by using a heterologous signal sequence. Therefore, in another embodiment, the fusion protein contains a heterologous signal sequence at its C- or N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52–58 (1995) and Johanson et al. *J. Biol. Chem.* 270:9459–9471). Thus, this invention also encompasses soluble fusion proteins containing an agmatinase polypeptide and various portions of the constant regions of heavy or light chains of immunoglobulins of various subclass (IgG, IgM, IgA, IgE). Preferred as immunoglobulin is the constant part of the heavy chain of human IgG, particularly IgGl, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). An agmatinase-encoding nucleic acid can be cloned into such an expression vector such that the fusion moiety is linked in-frame to the agmatinase.

Another form of fusion protein is one that directly affects agmatinase functions. Accordingly, an agmatinase polypeptide is encompassed by the present invention in which one or more of the agmatinase domains (or parts thereof) has been replaced by homologous domains (or parts thereof) from another agmatinase. Accordingly, various permutations are possible. For example, the binding or catalytic domain, or subregion thereof, can be replaced with the domain or subregion from another agmatinase or ureohydrolase. Thus, chimeric agmatinases can be formed in which one or more of the native domains or subregions has been replaced by another.

Additionally, chimeric agmatinase proteins can be produced in which one or more functional sites is derived from a different agmatinase isoform, or from another ureohydrolase. It is understood however that sites could be derived from other agmatinases that occur in the mammalian genome but which have not yet been discovered or characterized. Such sites include but are not limited to the catalytic site and binding sites for effectors or substrate, and other functional sites disclosed herein.

The isolated agmatinase can be purified from cells that naturally express it, such as from brain among others, especially purified from cells that have been altered to express it (recombinant) as shown in FIG. 5, or synthesized using known protein synthesis methods.

In one embodiment, the protein is produced by recombinant DNA techniques. For example, a nucleic acid molecule encoding the agmatinase polypeptide is cloned into an expression vector such as a yeast expression vector and the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (1990) *Meth. Enzymol.* 182: 626–646) and Rattan et al. (1992) *Ann. N.Y. Acad. Sci.* 663:48–62).

As is also well known, polypeptides are not always entirely linear. For instance, polypeptides may be branched as a result of ubiquitination, and they may be circular, with or without branching, generally as aresult of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli,* prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequence of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The agmatinase polypeptides are useful for producing antibodies specific for the agmatinase, regions, or fragments. Regions having a high antigenicity index score are shown in FIG. 2.

The agmatinase polypeptides are useful for biological assays related to agmatinase activity including but not limited to those disclosed in the background herein, such as hydrolysis of agmatine. Such assays involve any of the known agmatinase functions or activities or properties useful for diagnosis and treatment of agmatinase-related conditions, including putrescine and urea production and polyamine synthesis in general.

Figure 6:
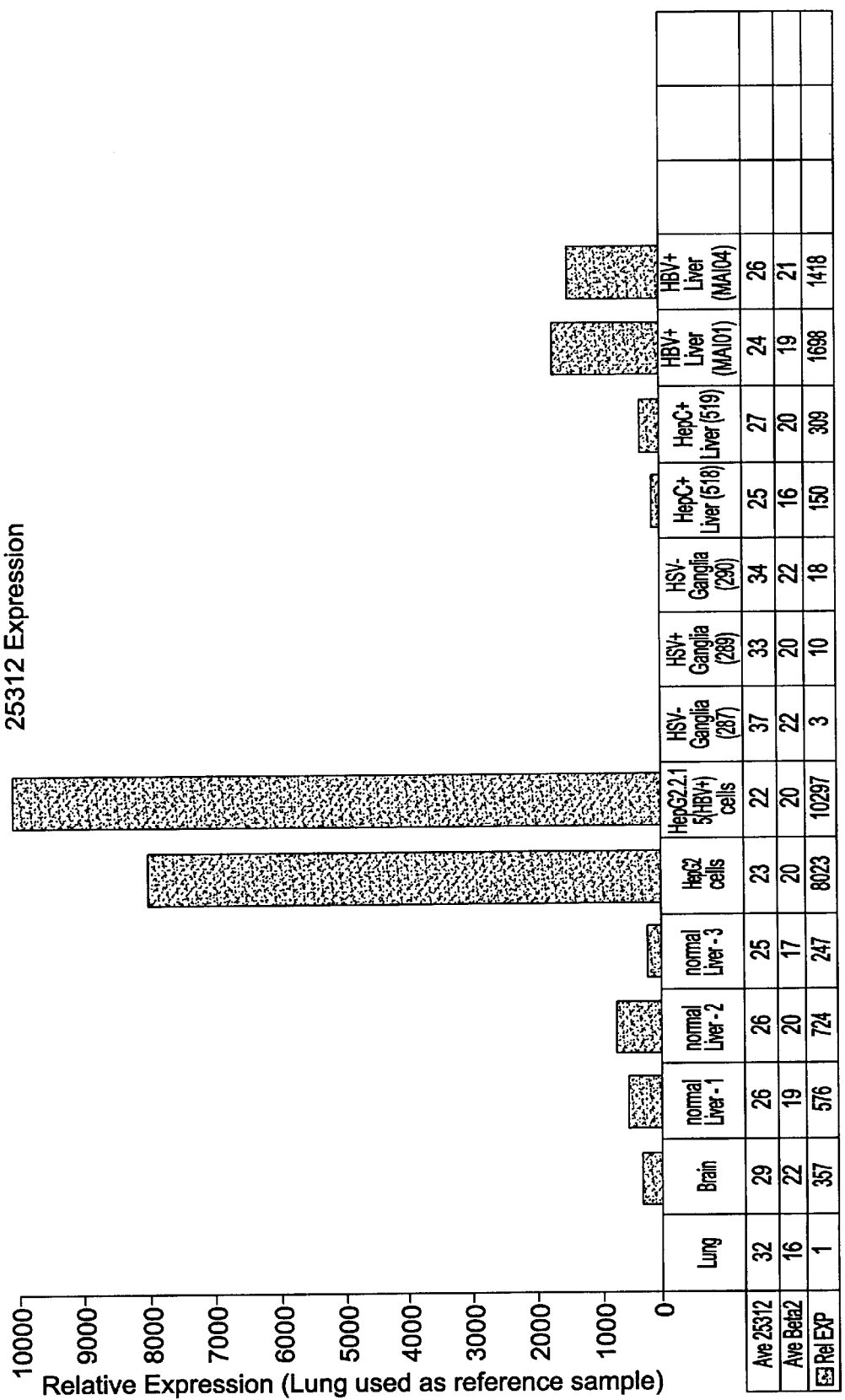
FIG. 6 shows expression of the human 25312 mRNA in various viral-infected and cultured cell lines using Taqman. The first five samples (from left) are normal or uninfected tissues; the next two samples are cultured HepG2 (transformed liver) cells and HepG2.2.15 (HepG2 expressing Hepatitis B virus [HBV]); the next three are human trigeminal ganglia tissue lacking (287) or containing (289 and 290) Herpes Simplex Virus (HSV), the next two are Hepatitis C Virus (HCV)-infected human liver; and the last two are HBV-infected human livers. This data shows that 25312 mRNA is more highly expressed in HBV- and HSV-infected tissues and cells compared to uninfected.

The agmatinase polypeptides are also useful in drug screening assays, in cell-based or cell-free systems. Cell-based systems can be native, i.e., cells that normally express the agmatinase, such as brain, as a biopsy or expanded in cell culture. In one embodiment, however, cell-based assays involve recombinant host cells expressing the agmatinase. FIG. 5 shows expression the 25312 agmatinase mRNA in various human tissues using Taqman (quantitative reverse transcriptase-PCR). In another embodiment, agmatinase is expressed in virally infected cells, including Hepatitis B virus, Hepatitis C virus, and Herpes Simplex virus (FIG. 6).

Determining the ability of the test compound to interact with the agmatinase can also comprise determining the ability of the test compound to preferentially bind to the polypeptide as compared to the ability of a known binding molecule (e.g., agmatine) to bind to the polypeptide.

The polypeptides can be used to identify compounds that modulate agmatinase activity. Such compounds, for example, can increase or decrease affinity or rate of binding to agmatine, compete with agmatine for binding to the agmatinase, or displace agmatine bound to the agmatinase. Both agmatinase and appropriate variants and fragments can be used in high-throughput screens to assay candidate compounds for the ability to bind to the agmatinase. These compounds can be further screened against a functional agmatinase to determine the effect of the compound on the agmatinase activity. Compounds can be identified that activate (agonist) or inactivate (antagonist) the agmatinase to a desired degree. Modulatory methods can be performed in vitro (e.g., by culturing the cell with the agent) or, alternatively, in vivo (e.g., by administering the agent to a subject).

The agmatinase polypeptides can be used to screen a compound for the ability to stimulate or inhibit interaction between the agmatinase protein and a target molecule that normally interacts with the agmatinase protein. The target can be agmatine (guanido-$^{14}$C agmatine) or other substrates that are guanidine derivatives of agmatine. Compounds containing an amino- or guanidine group at the position opposite to the guanidine end and possessing the hydrocarbon chain not less than $C_4$ are potential substrates for agmatinase (Vopr MedKhim (1976) 22(6):804–808).

Determining the ability of the agmatinase to bind to a target molecule can also be accomplished using a technology such as real-time Bimolecular Interaction Analysis (BIA). Sjolander et al. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 97:6378–6382); (Felici (1991) *J. Mol. Biol.* 222:301–310); (Ladner supra).

Candidate compounds include, for example, 1) peptides such as soluble peptides, including Ig-tailed fusion peptides and members of random peptide libraries (see, e.g., Lam et al. (1991) *Nature* 354:82–84; Houghten et al. (1991) *Nature* 354:84–86) and combinatorial chemistry-derived molecular libraries made of D- and/or L- configuration amino acids; 2) phosphopeptides (e.g., members of random and partially degenerate, directed phosphopeptide libraries, see, e.g., Songyang et al. (1993) *Cell* 72:767–778); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); 4) small organic and inorganic molecules (e.g., molecules obtained from combinatorial and natural product libraries); and 5) agmatine analogs.

One candidate compound is a soluble full-length agmatinase or fragment that competes for agmatine binding. Other candidate compounds include mutant agmatinases or appropriate fragments containing mutations that affect agmatinase function and thus compete for agmatine. Accordingly, a fragment that competes for agmatine, for example with a higher affinity, or a fragment that binds agmatine but does not hydrolyze it, is encompassed by the invention.

An assay for activity by means of a coupled urease system is disclosed in Carvajal et al., cited herein above, incorporated herein by reference for this assay (See, for example, page 197 of this reference). The invention further provides other end points to identify compounds that modulate (stimulate or inhibit) agmatinase activity. The assays typically involve an assay of events in the hydrolysis of agmatine that indicate agmatinase activity, such as discussed in the background hereinabove. For example, agmatinase activity can be determined in a two step procedure in which [$^{14}$C]urea and putrescine are produced; the [$^{14}$C]urea can then be hydrolyzed by a urease to $^{14}CO_2$ and $NH_3$ (Satishchandran, C. et al., (1986) *J. Bacteriology* 165: 843–848).

Also, the expression of genes that are up- or down-regulated in response to the agmatinase can be assayed. In one embodiment, the regulatory region of such genes can be operably linked to a marker that is easily detectable, such as luciferase.

Any of the biological or biochemical functions mediated by agmatinase can be used as an endpoint assay. These include all of the biochemical or biochemical/biological events described herein, in the references cited herein, incorporated by reference for these endpoint assay targets, and other functions known to those of ordinary skill in the art.

In the case of the agmatinase, specific end points can include putrescine and urea production and a decrease in agmatine.

Binding and/or activating compounds can also be screened by using chimeric agmatinase proteins in which one or more domains, sites, and the like, as disclosed herein, or parts thereof, can be replaced by their heterologous counterparts derived from other agmatinases.

The agmatinase polypeptides are also useful in competition binding assays in methods designed to discover compounds that interact with the agmatinase. Thus, a compound is exposed to an agmatinase polypeptide under conditions that allow the compound to bind or to otherwise interact with the polypeptide. Soluble agmatinase polypeptide is also added to the mixture. If the test compound interacts with the soluble agmatinase polypeptide, it decreases the amount of complex formed or activity from the agmatinase target. This type of assay is particularly useful in cases in which compounds are sought that interact with specific regions of the agmatinase. Thus, the soluble polypeptide that competes with the target agmatinase region is designed to contain peptide sequences corresponding to the region of interest.

Another type of competition-binding assay can be used to discover compounds that interact with specific functional sites and inhibit agmatinase. As an example, agmatine and a candidate compound can be added to a sample of the agmatinase. Compounds that interact with the agmatinase at the same site as the agmatine will reduce the amount of complex formed between the agmatinase and agmatine. One example of a compound that affects agmatinase activity is N-isoamylene agmatine (Khramov, V. (1965) *Vopr Med Khim* 22(6):804–808). Accordingly, it is possible to discover a compound that specifically prevents interaction between the agmatinase and agmatine. Another example involves adding a candidate compound to a sample of agmatinase and agmatine. A compound that competes with agmatine will reduce the amount of hydrolysis or binding of agmatine to the agmatinase. Accordingly, compounds can be discovered that directly interact with the agmatinase and compete with agmatine. Such assays can involve any other component that interacts with agmatinase to inhibit it, such as diethylpyrocarbonate (DEPC) (Carvajal, N. et al. (1999) *Biochem. Biophys. Res. Comm.* 264(1):196–200).

To perform cell free drug screening assays, it is desirable to immobilize either the agmatinase or agmatinase fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/agmatinase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of agmatinase binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of an agmatinase binding target component, such as butyrobetine, and a candidate compound are incubated in the agmatinase-presenting wells and the amount of complex trapped in the well can be quantitated. Methods for detecting such complexes, in addition to those described above for the GST-immobilized complexes, include immunodetection of complexes using antibodies reactive with the agmatinase target molecule, or which are reactive with agmatinase and compete with the target molecule; as well as enzyme-linked assays which rely on detecting an enzymatic activity associated with the target molecule.

Figure 7:
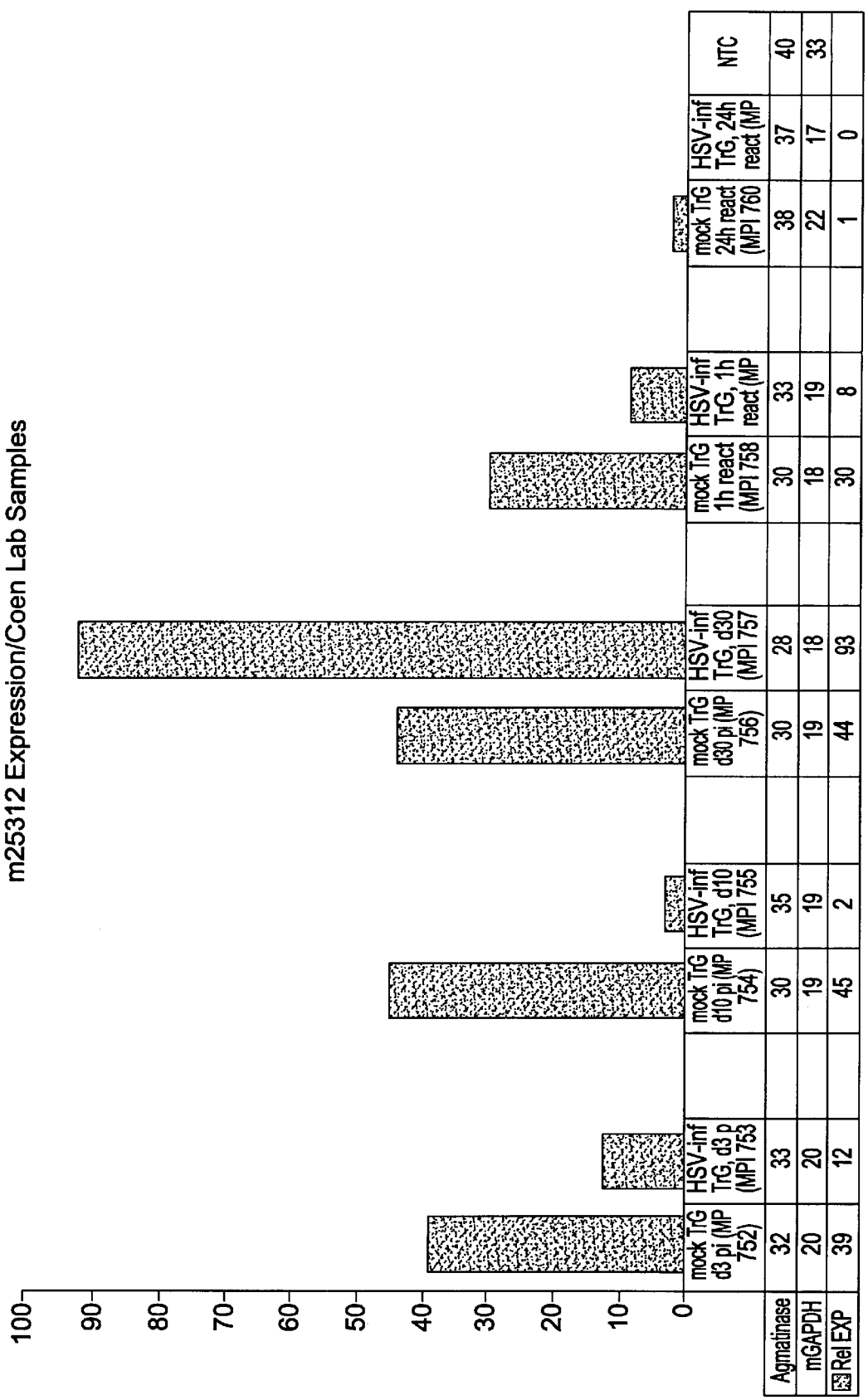
FIG. 7 shows expression of mouse 25312 in an in vivo model for HSV latency. At day 1, 30 mice were infected with HSV via the eyes, along with 30 "mock" infected mice. At day 3, 5 mice were sacrificed from each group and trigeminal ganglia (TrG) removed. TrG were removed from 5 mice of each group at day 10 and day 30. Also at day 30, TrG from 10 mice of each group were explanted into growth media, which are conditions that result in HSV reactivation from latency. The reactivating ganglia were harvested at either 1 or 24 hr. RNA was isolated from all TrG, and used for Taqman analysis of mouse 25312 expression. Results show that mouse 25312 mRNA is expressed at lower levels in HSV-infected TrG during periods of active HSV replication (day 3, day 10, and 1 h and 24 h reactivation), but is expressed at higher levels in TrG in which HSV is latent (day 30). Thus, 25312 expression appears to be induced during HSV latency.

Modulators of agmatinase activity identified according to these drug screening assays can be used to treat a subject with a disorder mediated by the agmatinase pathway, by treating cells that express the agmatinase, such as the brain and the other tissues herein described above in the background and shown in FIG. 5. Additionally, agmatinase may play an important role in the etiology of certain viral diseases, including but not limited to Hepatitis B and Herpes Simplex Virus (HSV). The enzyme which is induced during the latent phase of viral (HSV) infection and that the virus is priming neurons for agmatinase expression and concomitant high levels of polyamines in anticipation of reactivation from latency. The high levels of polyamine synthesis resulting from agmatinase production may be a general requirement for DNA viruses (FIGS. 6–7). Thus, modulators of agmatinase activity could be used to control viral diseases. The modulators can be used in the modulation, treatment and/or diagnosis of viral infected tissue or virus-associated tissue fibrosis, especially liver and liver fibrosis. Also, the agmatinase modulators can be used in the modulation, treatment and/or diagnosis of virus-associated carcinoma, especially hepatocellular cancer. These methods of treatment include the steps of administering the modulators of agmatinase activity in a pharmaceutical composition as described herein, to a subject in need of such treatment.

The gene is particularly relevant for the treatment of disorders involving the tissue in which the gene is expressed, and especially differentially expressed, including encephalopathy, cardiomyopathy, pulmonary distress, muscle weakness, myoglobolinaria, peripheral neuropathy, liver cirrhosis, brain dysfunction, spermatogenesis and fertility (Gilbert (1985) *Pathology* 17: 161–169).

Disorders in which agmatinase expression is relevant also include, but are not limited to, disease conditions associated with defective carnitine biosynthesis and fatty acid oxidation and involving heart failure, liver cirrhosis, kidney dysfunction, muscle fatigue, spermatogenesis, fertility, and brain dysfunction.

Moreover, modulators of agmatinase activity may be used to treat a wide variety of disorders in which agmatinase expression is relevant which may include but are not limited to neurotransmission in the central nervous system, pain perception and analgesia, cardiovascular myopathies, hypertension, inflammation and immune responses, cell proliferation in cancer, and viral replication in viral diseases.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromatosis, including Type 1 neurofibromatosis (NF1) and TYPE 2 neurofibromatosis (NF2), tuberous sclerosis, and Von Hippel-Lindau disease.

Agmatinase can have neurotransmitter activity. Accordingly, relevant disorders especially include disorders of neurotransmission, including, but not limited to, disorders of cognition, memory, movement, sensory functions, balance, and motor functions.

The agmatinase polypeptides are thus useful for treating an agmatinase-associated disorder characterized by aberrant expression or activity of an agmatinase. In one embodiment, the method involves administering an agent (e.g., an agent identified by a screening assay described herein), or combination of agents that modulates (e.g., upregulates or downregulates) expression or activity of the protein. In another embodiment, the method involves administering the agmatinase as therapy to compensate for reduced or aberrant expression or activity of the protein.

Methods for treatment include but are not limited to, use of soluble agmatinase or fragments of the agmatinase protein that compete for agmatine. These agmatinases or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer) or a disorder characterized by an aberrant hematopoietic response. In another example, it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins (captured proteins) which bind to or interact with the proteins of the invention and modulate their activity.

The agmatinase polypeptides also are useful to provide a target for diagnosing a disease or predisposition to disease mediated by the agmatinase, including, but not limited to, diseases involving tissues in which the agmatinase is expressed, such as those disclosed herein, and particularly in errors in polyamine biosynthesis. Accordingly, methods are provided for detecting the presence, or levels of, the agmatinase in a cell, tissue, or organism. The method involves contacting a biological sample with a compound capable of interacting with the agmatinase such that the interaction can be detected.

One agent for detecting agmatinase is an antibody capable of selectively binding to the polypeptide. A biological sample includes tissues, cells and biological fluids isolated from a subject, as well as tissues, cells and fluids present within a subject.

The agmatinase also provides a target for diagnosing active disease, or predisposition to disease, in a patient having a variant agmatinase. Thus, agmatinase can be isolated from a biological sample and assayed for the presence of a genetic mutation that results in an aberrant protein. This includes amino acid substitution, deletion, insertion, rearrangement (e.g., as the result of aberrant splicing events), and inappropriate post-translational modification. Analytic methods include altered electrophoretic mobility, altered tryptic peptide digest, altered agmatinase activity in cell-based or cell-free assays, alteration in agmatine hydrolysis, altered agmatine binding, or antibody-binding pattern, altered isoelectric point, direct amino acid sequencing, and any other of the known assay techniques useful for detecting mutations in a protein in general or in an agmatinase specifically.

In vitro techniques for detection of agmatinase include enzyme linked immunosorbent assays (ELISAs), Western blots, irnnunoprecipitations and immunofluorescence. Alternatively, the protein can be detected in vivo in a subject by introducing into the subject a labeled anti-agmatinase antibody. For example, the antibody can be labeled with a radioactive marker whose presence and location in a subject can be detected by standard imaging techniques. Particularly useful are methods, which detect the allelic variant of the agmatinase expressed in a subject, and methods, which detect fragments of the agmatinase in a sample.

The agmatinase polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) *Clin. Exp. Phannacol. Physiol.* 23(10–11):983–985, and Linder, M. W. (1997) *Clin. Chem.* 43(2):254–266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the agmatinase in which one or more of the agmatinase functions in one population is different from those in another population. The polypeptides thus provide a target to ascertain a genetic predisposition that can affect treatment modality.

The agmatinase polypeptides are also useful for monitoring therapeutic effects during clinical trials and other treatment. Thus, the therapeutic effectiveness of an agent that is designed to increase or decrease gene expression, protein levels or agmatinase activity can be monitored over the course of treatment using the agmatinase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the agmatinase and its variants and fragments. An antibody is considered to selectively bind, even if it also binds to other proteins that are not substantially homologous with the agmatinase. These other proteins share homology with a fragment or domain of the agmatinase. This conservation in specific regions gives rise to antibodies that bind to both proteins by virtue of the homologous sequence. In this case, it would be understood that antibody binding to the agmatinase is still selective.

To generate antibodies, an isolated agmatinase polypeptide is used as an immunogen to generate antibodies using standard techniques for polyclonal and monoclonal antibody preparation. Either the full-length protein or antigenic peptide fragment can be used. Regions having a high antigenicity index are shown in FIG. 2.

Antibodies are preferably prepared from these regions or from discrete fragments in these regions. However, antibodies can be prepared from any region of the peptide as described herein. A preferred fragment produces an antibody that diminishes or completely prevents agmatine binding. Antibodies can be developed against the entire agmatinase or domains of the agmatinase as described herein. Antibodies can also be developed against specific functional sites as disclosed herein.

The antigenic peptide can comprise a contiguous sequence of at least 5, 10, 15, 20, 20–25, 25–30 or more amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

An appropriate immunogenic preparation can be derived from native, recombinantly expressed, or chemically synthesized peptides.

Antibody Uses

The antibodies can be used to isolate an agmatinase by standard techniques, such as affinity chromatography or immunoprecipitation. The antibodies can facilitate the purification of the natural agmatinase from cells and recombinantly produced agmatinase expressed in host cells.

The antibodies are useful to detect the presence of agmatinase in cells or tissues to determine the pattern of expression of the agmatinase among various tissues in an organism and over the course of normal development.

The antibodies can be used to detect agmatinase in situ, in vitro, or in a cell lysate or supernatant in order to evaluate the abundance and pattern of expression.

The antibodies can be used to assess abnormal tissue distribution or abnormal expression during development.

Antibody detection of circulating fragments of the fall length agmatinase can be used to identify agmatinase turnover.

Further, the antibodies can be used to assess agmatinase expression in disease states such as in active stages of the disease or in an individual with a predisposition toward disease related to agmatinase function. When a disorder is caused by an inappropriate tissue distribution, developmental expression, or level of expression of the agmatinase protein, the antibody can be prepared against the normal agmatinase protein. If a disorder is characterized by a specific mutation in the agmatinase, antibodies specific for this mutant protein can be used to assay for the presence of the specific mutant agmatinase. However, intracellularly-made antibodies ("intrabodies") are also encompassed, which would recognize intracellular agmatinase peptide regions.

The antibodies can also be used to assess normal and aberrant subcellular localization of cells in the various tissues in an organism. Antibodies can be developed against the whole agmatinase or portions of the agmatinase.

The diagnostic uses can be applied, not only in genetic testing, but also in monitoring a treatment modality. Accordingly, where treatment is ultimately aimed at correcting agmatinase expression level or the presence of aberrant agmatinase and aberrant tissue distribution or developmental expression, antibodies directed against the agmatinase or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic agmatinase can be used to identify individuals that require modified treatment modalities.

The antibodies are also useful as diagnostic tools as an immunological marker for aberrant agmatinase analyzed by electrophoretic mobility, isoelectric point, tryptic peptide digest, and other physical assays known to those in the art.

The antibodies are also useful for tissue typing. Thus, where a specific agmatinase has been correlated with expression in a specific tissue, antibodies that are specific for this agmatinase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for agmatinase function, for example, blocking agmatine binding.

These uses can also be applied in a therapeutic context in which treatment involves inhibiting agmatinase function. An antibody can be used, for example, to block agmatine binding. Antibodies can be prepared against specific fragments containing sites required for function or against intact agmatinase associated with a cell.

Completely human antibodies are particularly desirable for therapeutic treatment of human patients. For an overview of this technology for producing human antibodies, see Lonberg et al. (1995) *Int. Rev. Immunol.* 13:65–93. For a detailed discussion of this technology for producing human antibodies and human monoclonal antibodies and protocols for producing such antibodies, e.g., U.S. Pat. Nos. 5,625,126; 5,633,425; 5,569,825; 5,661,016; and U.S. Pat. No. 5,545,806.

The invention also encompasses kits for using antibodies to detect the presence of an agmatinase protein in a biological sample. The kit can comprise antibodies such as a labeled or labelable antibody and a compound or agent for detecting agmatinase in a biological sample; means for determining the amount of agmatinase in the sample; and means for comparing the amount of agmatinase in the sample with a standard. The compound or agent can be packaged in a suitable container. The kit can further comprise instructions for using the kit to detect agmatinase.

Polynucleotides

The nucleotide sequences in SEQ ID NO: 2 were obtained by sequencing the deposited human cDNA. Accordingly, the sequence of the deposited clone is controlling as to any discrepancies between the two and any reference to the sequence of SEQ ID NO:2 includes reference to the sequence of the deposited cDNA.

The specifically disclosed cDNA comprises the coding region and 5' and 3' untranslated sequences in SEQ ID NO:2. In one embodiment, the agmatinase nucleic acid compromises only the coding region.

The invention provides isolated polynucleotides encoding the novel agmatinase. The term "agmatinase polynucleotide" or "agmatinase nucleic acid" refers to the sequence shown in SEQ ID NO 2 or in the deposited cDNA. The term "agmatinase polynucleotide" or "agmatinase nucleic acid" further includes variants and fragments of the agmatinase polynucleotide.

An "isolated" agmatinase nucleic acid is one that is separated from other nucleic acid present in the natural source of the agmatinase nucleic acid. Preferably, an "isolated" nucleic acid is free of sequences which naturally flank the agmatinase nucleic acid (i.e., sequences located at the 5' and 3' ends of the nucleic acid) in the genomic DNA of the organism from which the nucleic acid is derived. However, there can be some flanking nucleotide sequences, for example up to about 5KB. The important point is that the agmatinase nucleic acid is isolated from flanking sequences such that it can be subjected to the specific manipulations described herein, such as recombinant expression, preparation of probes and primers, and other uses specific to the agmatinase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The agmatinase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The agmatinase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Agmatinase polynucleotides can be in the form of RNA, such as mRNA, or in the form of DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides variant agmatinase polynucleotides, and fragments thereof, that differ from the nucleotide sequence shown in SEQ ID NO:2 due to degeneracy of the genetic code and thus encode the same protein as that encoded by the nucleotide sequence shown in SEQ ID NO:2.

The invention also provides agmatinase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with the nucleic acid molecule of SEQ ID NO: 2 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding an agmatinase that is at least about 50–55%, 55–60%, 60–65%, 65–70%, typically at least about 70–75%, more typically at least about 80–85%, and most typically at least about 90–95% or more homologous to the nucleotide sequence shown in SEQ ID NO: 2 or a fragment of this sequence. Such nucleic acid molecules can readily be identified as being able to hybridize under stringent conditions, to the nucleotide sequence shown in SEQ ID NO:2 or a fragment of the sequence. It is understood that stringent hybridization does not indicate substantial homology where it is due to general homology, such as poly A sequences, or sequences common to all or most proteins, all agmatinases or other ureohydrolases. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 60–65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in Current Protocols in Molecular Biology, John Wiley & Sons, N.Y. (1989), 6.3.1–6.3.6, incorporated by reference. One example of stringent hybridization conditions are hybridization in 6x sodium chloride/sodium citrate (SSC) at about 45° C., followed by one or more washes in 0.2xSSC, 0.1% SDS at 50–65° C. In another non-limiting example, nucleic acid molecules are allowed to hybridize in 6x sodium chloride/sodium citrate (SSC) at about 45° C., followed by one or more low stringency washes in 0.2x SSC/0.1% SDS at room temperature, or by one or more moderate stringency washes in 0.2xSSC/0.1% SDS at 42° C., or washed in 0.2xSSC/0.1% SDS at 65° C. for high stringency. In one embodiment, an isolated nucleic acid molecule that hybridizes under stringent conditions to the sequence of SEQ ID NO: 1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

Furthermore, the invention provides polynucleotides that comprise a fragment of the full-length agmatinase polynucleotide. The fragment can be single or double-stranded and can comprise DNA or RNA. The fragment can be derived from either the coding or the non-coding sequence.

The present invention also provides isolated nucleic acids that contain a single or double stranded fragment or portion that hybridizes under stringent conditions to the nucleotide sequence of SEQ ID NO:2 or the complement of SEQ ID NO:2. In one embodiment, the nucleic acid consists of a portion of the nucleotide sequence of SEQ ID NO:2 or the complement of SEQ ID NO:2. The nucleic acid fragments of the invention are at least about 10–15, preferably at least about 16, 17, 18, 19, 20, 23 or 25 contiguous nucleotides, and can be 30, 40, 50, 60, 70, 80, 90, 100, 200, 500 or more nucleotides in length. Longer fragments, for example, 600 or more nucleotides in length, which encode antigenic proteins or polypeptides described herein are useful.

In certain embodiments, fragments are as follows: from nucleotide 1 to about nucleotide 1012, fragments are at least 5–10 contiguous nucleotides in length. From about nucleotide 1538 to about nucleotide 1700, fragments are about at least 5–10 nucleotides in length. From about nucleotide 1012 to about nucleotide 1700, fragments are about at least 5–10 nucleotides in length.

In another embodiment an isolated agmatinase nucleic acid encodes the entire coding region. Other fragments include nucleotide sequences encoding the amino acid fragments described herein.

Thus, agmatinase nucleic acid fragments further include sequences corresponding to the domains described herein, subregions also described, and specific functional sites. Agmatinase nucleic acid fragments also include combinations of the domains, segments, and other functional sites described above. It is understood that an agmatinase fragment includes any nucleic acid sequence that does not include the entire gene. A person of ordinary skill in the art would be aware of the many permutations that are possible.

Where the location of the domains or sites have been predicted by computer analysis, one of ordinary skill would appreciate that the amino acid residues constituting these domains can vary depending on the criteria used to define the domains.

However, it is understood that an agmatinase fragment includes any nucleic acid sequence that does not include the entire gene.

The invention also provides agmatinase nucleic acid fragments that encode epitope bearing regions of the agmatinase proteins described herein.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403–10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497–1500. Typically, a probe comprises a region of nucleotide sequence that hybridizes under highly stringent conditions to at least about 15, typically about 20–25, and more typically about 30, 40 or 50 consecutive nucleotides of the nucleic acid sequence shown in SEQ ID NO:2 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The agmatinase polynucleotides are thus useful for probes, primers, and in biological assays.

Where the polynucleotides are used to assess agmatinase properties or functions, such as in the assays described herein, all or less than all of the entire cDNA can be useful. Assays specifically directed to agmatinase functions, such as assessing agonist or antagonist activity, encompass the use of known fragments. Further, diagnostic methods for assessing agmatinase function can also be practiced with any fragment, including those fragments that may have been known prior to the invention. Similarly, in methods involving treatment of agmatinase dysfunction, all fragments are encompassed including those, which may have been known in the art.

The agmatinase polynucleotides are useful as a hybridization probe for cDNA and genomic DNA to isolate a full-length cDNA and genomic clones encoding the polypeptide described in SEQ ID NO 1 and to isolate cDNA and genonlic clones that correspond to variants producing the same polypeptide shown in SEQ ID NO 1 or the other variants described herein. Variants can be isolated from the same tissue and organism from which the polypeptide shown in SEQ ID NO 1 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the agmatinase. Accordingly, it could be derived from 5' noncoding region, the coding region, and 3' noncoding region.

The nucleic acid probe can be, for example, the full-length cDNA of SEQ ID NO: 2, or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequences of SEQ ID NO 2, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357–63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell agmatinase in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm Res.* 5:539–549).

The agmatinase polynucleotides are also useful as primers for PCR to amplify any given region of an agmatinase polynucleotide.

The agmatinase polynucleotides are also useful for constructing recombinant vectors. Such vectors include expression vectors that express a portion of, or all of, the agmatinase polypeptides. Vectors also include insertion vectors, used to integrate into another polynucleotide sequence, such as into the cellular genome, to alter in situ expression of agmatinase genes and gene products. For example, an endogenous agmatinase coding sequence can be replaced via homologous recombination with all or part of the coding region containing one or more specifically introduced mutations.

The agmatinase polynucleotides are also useful for expressing antigenic portions of the agmatinase proteins.

The agmatinase polynucleotides are also useful as probes for determining the chromosomal positions of the agmatinase polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man,* available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783–787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The agmatinase polynucleotide probes are also useful to determine patterns of the presence of the gene encoding the agmatinases and variants with respect to tissue distribution, for example, whether gene duplication has occurred and whether the duplication occurs in all or only a subset of tissues. The genes can be naturally occurring or can have been introduced into a cell, tissue, or organism exogenously.

The agmatinase polynucleotides are also useful for designing ribozymes corresponding to all, or a part, of the mRNA produced from genes encoding the polynucleotides described herein.

The agmatinase polynucleotides are also useful for constructing host cells expressing a part, or all, of the agmatinase polynucleotides and polypeptides.

The agmatinase polynucleotides are also useful for constructing transgenic animals expressing all, or a part, of the agmatinase polynucleotides and polypeptides.

The agmatinase polynucleotides are also useful for making vectors that express part, or all, of the agmatinase polypeptides.

The agmatinase polynucleotides are also useful as hybridization probes for determining the level of agmatinase nucleic acid expression. Accordingly, the probes can be used to detect the presence of, or to determine levels of, agmatinase nucleic acid in cells, tissues, and in organisms. The nucleic acid can be DNA or RNA. Accordingly, probes corresponding to the polypeptides described herein can be used to assess gene copy number in a given cell, tissue, or organism. This is particularly relevant in cases in which there has been an amplification of the agmatinase genes.

Alternatively, the probe can be used in an in situ hybridization context to assess the position of extra copies of the agmatinase genes, as on extrachromosomal elements or as integrated into chromosomes in which the agmatinase gene is not normally found, for example as a homogeneously staining region.

These uses are relevant for diagnosis of disorders involving an increase or decrease in agmatinase expression relative to normal, such as a proliferative disorder, a differentiative or developmental disorder, or a hematopoietic disorder, or any other disorder involving polyamine deficiency, especially involving the tissues herein described.

Disorders in which agmatinase expression is relevant also include, but are not limited to, disease conditions associated with defective carnitine biosynthesis and fatty acid oxidation and involving heart failure, liver cirrhosis, kidney dysfumction, muscle fatigue, spermatogenesis, fertility, and brain dysfunction.

Thus, the present invention provides a method for identifying a disease or disorder associated with aberrant expression or activity of agmatinase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mnRNA include Northern hybridizations and in situ hybridizations. In vitro techniques for detecting DNA includes Southern hybridizations and in situ hybridization.

Probes can be used as a part of a diagnostic test kit for identifying cells or tissues that express the agmatinase, such as by measuring the level of an agmatinase-encoding nucleic acid in a sample of cells from a subject e.g., mRNA or genomic DNA, or determining if the agmatinase gene has been mutated.

Nucleic acid expression assays are useful for drug screening to identify compounds that modulate agmatinase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the agent to a subject) in patients or in transgenic animals.

The invention thus provides a method for identifying a compound that can be used to treat a disorder associated with nucleic acid expression of the agmatinase gene. The method typically includes assaying the ability of the compound to modulate the expression of the agmatinase nucleic acid and thus identifying a compound that can be used to treat a disorder characterized by undesired agmatinase nucleic acid expression.

The assays can be performed in cell-based and cell-free systems. Cell-based assays include cells naturally expressing the agmatinase nucleic acid or recombinant cells genetically engineered to express specific nucleic acid sequences.

Alternatively, candidate compounds can be assayed in vivo in any subject, including patients, or in transgenic animals.

The assay for agmatinase nucleic acid expression can involve direct assay of nucleic acid levels, such as mRNA levels, or on collateral compounds involved in the carnitine biosynthetic pathway. Further, the expression of genes that are up- or down-regulated in response to the agmatinase pathway can also be assayed. In this embodiment the regulatory regions of these genes can be operably linked to a reporter gene such as luciferase.

Thus, modulators of agmatinase gene expression can be identified in a method wherein a cell is contacted with a candidate compound and the expression of mRNA determined. The level of expression of agmatinase mRNA in the presence of the candidate compound is compared to the level of expression of agmatinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The gene is particularly relevant for the treatment of disorders involving the tissue in which the gene is expressed, and especially differentially expressed, including encephalopathy, cardiomyopathy, pulmonary distress, muscle weakness, myoglobolinaria, peripheral neuropathy, liver cirrhosis, brain dysfunction, spermatogenesis and fertility (Gilbert (1985) *Pathology* 17: 161–169).

Accordingly, the invention provides methods of treatment, with the nucleic acid as a target, using a compound identified through drug screening as a gene modulator to modulate agmatinase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid.

Alternatively, a modulator for agmatinase nucleic acid expression (level or activity) can be a small molecule or drug identified using the screening assays described herein as long as the drug or small molecule increases or inhibits the agmatinase nucleic acid expression.

The agmatinase polynucleotides are also useful for monitoring the effectiveness of modulating compounds on the expression of the agmatinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified MRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The agmatinase polynucleotides are also useful in diagnostic assays for qualitative changes in agmatinase nucleic acid, and particularly in qualitative changes that lead to pathology. The polynucleotides can be used to detect mutations in agmatinase genes and gene expression products such as mRNA. The polynucleotides can be used as hybridization probes to detect naturally-occurring genetic mutations in the agmatinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the agmatinase gene associated with a dysfunction provides a diagnostic tool for an active disease or susceptibility to disease when the disease results from overexpression, underexpression, or altered expression of an agmatinase.

Mutations in the agmatinase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size ofthe amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in an agmatinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant agmatinase gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol* 38: 147–159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton et al. (1993) *Mutat. Res.* 285:125–144; and Hayashi et al. (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991)

*Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244–255; Kozal et al. (1996) *Nature Medicine* 2:753–759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The agmatinase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the agmatinase gene that results in altered affinity for agmatine could result in an excessive or decreased drug effect with standard concentrations of agmatine (or analog) that activates the agmatinase. Accordingly, the agmatinase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The agmatinase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The agmatinase polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the agmatinase sequence can be used to provide an alternative technique, which determines the actual DNA sequence of selected fragments in the genome of an individual. Thus, the agmatinase sequence described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The agmatinase sequence can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The agmatinase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The agmatinase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The agmatinase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of agmatinase probes can be used to identify tissue by species and/or by organ type.

In a similar fashion, these primers and probes can be used to screen tissue culture for contamination (i.e. screen for the presence of a mixture of different types of cells in a culture).

Alternatively, the agmatinase polynucleotides can be used directly to block transcription or translation of agmatinase gene sequences by means of antisense or ribozyme constructs. Thus, in a disorder characterized by abnormally high or undesirable agmatinase gene expression, nucleic acids can be directly used for treatment.

The agmatinase polynucleotides are thus useful as antisense constructs to control agmatinase gene expression in cells, tissues, and organisms. A DNA antisense polynucleotide is designed to be complementary to a region of the gene involved in transcription, preventing transcription and hence production of agmatinase protein. An antisense RNA or DNA polynucleotide would hybridize to the mRNA and thus block translation of mRNA into agmatinase protein.

Examples of antisense molecules useful to inhibit nucleic acid expression include antisense molecules complementary to a fragment of the 5' untranslated region of SEQ ID NO:2 which also includes the start codon and antisense molecules which are complementary to a fragment of the 3' untranslated region of SEQ ID NO:2.

Alternatively, a class of antisense molecules can be used to inactivate mRNA in order to decrease expression of agmatinase nucleic acid. Accordingly, these molecules can treat a disorder characterized by abnormal or undesired agmatinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the binding, catalytic, and other functional activities of the agmatinase protein.

The agmatinase polynucleotides also provide vectors for gene therapy in patients containing cells that are aberrant in agmatinase gene expression. Thus, recombinant cells, which include the patient's cells that have been engineered ex vivo and returned to the patient, are introduced into an individual where the cells produce the desired agmatinase protein to treat the individual.

The invention also encompasses kits for detecting the presence of an agmatinase nucleic acid in a biological sample. For example, the kit can comprise reagents such as a labeled or labelable nucleic acid or agent capable of detecting agmatinase nucleic acid in a biological sample; means for determining the amount of agmatinase nucleic acid in the sample; and means for comparing the amount of agmatinase nucleic acid in the sample with a standard. The compound or agent can be packaged in a suitable container. The kit can further comprise instructions for using the kit to detect agmatinase mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the agmatinase polynucleotides. The term "vector" refers to a vehicle, preferably a nucleic acid molecule that can transport the agmatinase polynucleotides. When the vector is a nucleic acid molecule, the agmatinase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the agmatinase polynucleotides. Alternatively, the vector may integrate into the host cell genome and produce additional copies of the agmatinase polynucleotides when the host cell replicates.

The invention provides vectors for the maintenance (cloning vectors) or vectors for expression (expression vectors) of the agmatinase polynucleotides. The vectors can function in procaryotic or eukaryotic cells or in both (shuttle vectors).

Expression vectors contain cis-acting regulatory regions that are operably linked in the vector to the agmatinase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the agmatinase polynucleotides from the vector. Alternatively, a trans-acting factor may be supplied by the host cell. Finally, a trans-acting factor can be produced from the vector itself.

It is understood, however, that in some embodiments, transcription and/or translation of the agmatinase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual 2nd. ed.,* Cold Spring Harbor Laboratory Press, Cold Spring Harbor, N.Y.).

A variety of expression vectors can be used to express an agmatinase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual 2nd. ed.,* Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The agmatinase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli,* Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the polypeptide as a fusion protein. Accordingly, the invention provides fusion vectors that allow for the production of the agmatinase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301–315) and pET 11d (Studier et al. (1990) *Gene Expression Technology: Methods in Enzymology* 185:60–89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119–128). Alternatively, the sequence of the polynucleotide of interest can be altered to provide preferential codon usage for a specific host cell, for example *E. coli*. (Wada et al. (1992) *Nucleic Acids Res.* 20:2111–2118).

The agmatinase polynucleotides can also be expressed by expression vectors that are operative in yeast. Examples of vectors for expression in yeast e.g., *S. cerevisiae* include pYepSec1 (Baldari et al. (1987) *EMBO J.* 6:229–234), pMFa (Kurjan et al. (1982) *Cell* 30:933–943), pJRY88 (Schultz et al. (1987) *Gene* 54:113–123), and pYES2 (Invitrogen Corporation, San Diego, Calif.).

The agmatinase polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow et al. (1989) *Virology* 170:31–39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187–195).

The expression vectors listed herein are provided by way of example only of the well-known vectors available to those of ordinary skill in the art that would be useful to express the agmatinase polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual 2nd, ed., Cold Spring Harbor Laboratory,* Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual,* 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the agmatinase polynucleotides can be introduced either alone or with other polynucleotides that are not related to the agmatinase polynucleotides such as those providing transacting factors for expression vectors. When more than one vector is introduced into a cell, the vectors can be introduced independently, co-introduced orjoined to the agmatinase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the agmatinase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing agmatinase proteins or polypeptides that can be furter purified to produce desired amounts of agmatinase protein or fragments. Thus, host cells containing expression vectors are useful for polypeptide production.

Host cells are also useful for conducting cell-based assays involving the agmatinase or agmatinase fragments. Thus, a recombinant host cell expressing a native agmatinase is useful to assay for compounds that stimulate or inhibit agmatinase function.

Host cells are also useful for identifying agmatinase mutants in which these functions are affected. If the mutants naturally occur and give rise to a pathology, host cells containing the mutations are useful to assay compounds that have a desired effect on the mutant agmatinase (for example, stimulating or inhibiting function) which may not be indicated by their effect on the native agmatinase.

Recombinant host cells are also useful for expressing the chimeric polypeptides described herein to assess compounds that activate or suppress activation by means of a heterologous domain, segment, site, and the like, as disclosed herein.

Further, mutant agmatinases can be designed in which one or more of the various functions is engineered to be increased or decreased (e.g., agmatine binding) and used to augment or replace agmatinase proteins in an individual. Thus, host cells can provide a therapeutic benefit by replacing an aberrant agmatinase or providing an aberrant agmatinase that provides a therapeutic result. In one embodiment, the cells provide agmatinase that is abnormally active.

In another embodiment, the cells provide agmatinases that are abnormally inactive. These agmatinases can compete with endogenous agmatinases in the individual.

In another embodiment, cells expressing agmatinase that cannot be activated, are introduced into an individual in order to compete with endogenous agmatinase for agmatine. For example, in the case in which excessive agmatine (or analog) is part of a treatment modality, it may be necessary to inactivate this molecule at a specific point in treatment. Providing cells that compete for the molecule, but which cannot be affected by agmatinase activation would be beneficial.

Homologously recombinant host cells can also be produced that allow the in situ alteration of endogenous agmatinase polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat Nos. 5,272,071, and 5,641,670. Briefly, specific polynucleotide sequences corresponding to the agmatinase polynucleotides or sequences proximal or distal to an agmatinase gene are allowed to integrate into a host cell genome by homologous recombination where expression of the gene can be affected. In one embodiment, regulatory sequences are introduced that either increase or decrease expression of an endogenous sequence.

Accordingly, an agmatinase protein can be produced in a cell not normally producing it. Alternatively, increased expression of agmatinase protein can be effected in a cell normally producing the protein at a specific level. Further, expression can be decreased or eliminated by introducing a specific regulatory sequence. The regulatory sequence can be heterologous to the agmatinase protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant agmatinase proteins. Such mutations could be introduced, for example, into the specific functional regions such as the substrate binding site.

In one embodiment, the host cell can be a fertilized oocyte or embryonic stem cell that can be used to produce a transgenic animal containing the altered agmatinase gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous agmatinase gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinions in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of an agmatinase protein and identifying and evaluating modulators of agmatinase protein activity.

Other examples of transgenic animals include non-human primates, sheep, dogs, cows, goats, chickens, and amphibians.

In one embodiment, a host cell is a fertilized oocyte or an embryonic stem cell into which an agmatinase polynucleotide sequence has been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any agmatinase nucleotide sequence can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the agmatinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect agmatine binding and hydrolysis and polyamine biosynthesis, may not be evident from in vitro cell-free or cell-based assays. Accordingly, it is useful to provide non-human transgenic animals to assay in vivo agmatinase function, including agmatine interaction, the effect of specific mutant ureohydrolases on agmatinase function and agmatine interaction, and the effect of chimeric agmatinases. It is also possible to assess the effect of null mutations, that is mutations that substantially or completely eliminate one or more agmatinase functions.

In general, methods for producing transgenic animals include introducing a nucleic acid sequence according to the present invention, the nucleic acid sequence capable of expressing the protein in a transgenic animal, into a cell in culture or in vivo. When introduced in vivo, the nucleic acid is introduced into an intact organism such that one or more cell types and, accordingly, one or more tissue types, express the nucleic acid encoding the protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

The agmatinase nucleic acid molecules, proteins, modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an agmatinase protein or anti-agmatinase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms ofthe invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

That which is claimed:

1. An isolated nucleic acid molecule selected from the group consisting of:
   a) a nucleic acid molecule comprising the nucleotide sequence of SEQ ID NO:2, the cDNA insert of the plasmid deposited with ATCC as Accession Number PTA-1844, or a complement thereof; and,
   b) a nucleic acid molecule which encodes a polypeptide comprising the amino acid sequence of SEQ ID NO:1 or a polypeptide encoded by the cDNA insert of the plasmid deposited with ATCC as Accession Number PTA-1844, or a complement thereof.

2. The nucleic acid molecule of claim 1 further comprising vector nucleic acid sequences.

3. The nucleic acid molecule of claim 1 further comprising nucleic acid sequences encoding a heterologous polypeptide.

4. A host cell which contains the nucleic acid molecule of claim 2.

5. The host cell of claim 4 which is a mammalian host cell.

6. A nonhuman mammalian host cell containing the nucleic acid molecule of claim 2.

7. A method for producing a polypeptide comprising the amino acid sequence of SEQ ID NO:1, or an amino acid sequence encoded by the cDNA insert of the plasmid deposited with ATCC as Accession Number PTA-1844;
   said method comprising culturing the host cell of claim 4 under conditions in which the nucleic acid molecule is expressed and isolating said polypeptide.

8. A kit comprising a nucleic acid molecule of claim 1 and instructions for use of said nucleic acid molecule as a hybridization probe under stringent conditions, said stringent conditions comprising hybridization in 6× sodium chloride/sodium citrate (SSC) at about 45° C., followed by one or more washes in 0.2×SSC, 0.1% SDS at 65° C.

9. An isolated nucleic acid molecule having at least 95% sequence identity to the nucleotide sequence of SEQ ID NO:2, wherein said nucleic acid molecule encodes a polypeptide having agmatinase activity.

* * * * *

UNITED STATES PATENT AND TRADEMARK OFFICE
CERTIFICATE OF CORRECTION

PATENT NO. : 6,413,757 B1
DATED : July 2, 2002
INVENTOR(S) : Cook et al.

It is certified that error appears in the above-identified patent and that said Letters Patent is hereby corrected as shown below:

<u>Title page,</u>
Item [73], Assignee: add -- ; Bayer Corporation, Pittsburgh, PA (US) --.

<u>Column 5,</u>
Line 56, "agriatinase" should read -- agmatinase --.

Signed and Sealed this

Eighth Day of April, 2003

JAMES E. ROGAN
*Director of the United States Patent and Trademark Office*

SEQUENCE LISTING

```
<160> NUMBER OF SEQ ID NOS:  2

<210> SEQ ID NO 1
<211> LENGTH: 352
<212> TYPE: PRT
<213> ORGANISM: Homo sapiens

<400> SEQUENCE: 1

Met Leu Arg Leu Leu Ala Ser Gly Cys Ala Arg Gly Pro Gly Pro Gly
 1               5                  10                  15

Val Gly Ala Arg Pro Ala Ala Gly Leu Phe His Pro Gly Arg Arg Gln
            20                  25                  30

Ser Arg Gln Ala Ser Asp Ala Pro Arg Asn Gln Pro Pro Ser Pro Glu
        35                  40                  45

Phe Val Ala Arg Pro Val Gly Val Cys Ser Met Met Arg Leu Pro Val
    50                  55                  60

Gln Thr Ser Pro Glu Gly Leu Asp Ala Ala Phe Ile Gly Val Pro Leu
65                  70                  75                  80

Asp Thr Gly Thr Ser Asn Arg Pro Gly Ala Arg Phe Gly Pro Arg Arg
                85                  90                  95
```

```
Ile Arg Glu Glu Ser Val Met Leu Gly Thr Val Asn Pro Ser Thr Gly
            100                 105                 110

Ala Leu Pro Phe Gln Ser Leu Met Val Ala Asp Leu Gly Asp Val Asn
            115                 120                 125

Val Asn Leu Tyr Asn Leu Gln Asp Ser Cys Arg Arg Ile Gln Glu Ala
130                 135                 140

Tyr Glu Lys Ile Val Ala Ala Gly Cys Ile Pro Leu Thr Leu Gly Gly
145                 150                 155                 160

Asp His Thr Ile Thr Tyr Pro Ile Leu Gln Ala Met Ala Lys Lys His
                165                 170                 175

Gly Pro Val Gly Leu Leu His Val Asp Ala His Thr Asp Thr Thr Asp
                180                 185                 190

Lys Ala Leu Gly Glu Lys Leu Tyr His Gly Ala Pro Phe Arg Arg Cys
            195                 200                 205

Val Asp Glu Gly Leu Leu Asp Cys Lys Arg Val Gln Ile Gly Ile
210                 215                 220

Arg Gly Ser Ser Thr Thr Leu Asp Pro Tyr Arg Tyr Asn Arg Ser Gln
225                 230                 235                 240

Gly Phe Arg Val Val Leu Ala Glu Asp Cys Trp Met Lys Ser Leu Val
                245                 250                 255

Pro Leu Met Gly Glu Val Arg Gln Gln Met Gly Lys Pro Ile Tyr
            260                 265                 270

Ile Ser Phe Asp Ile Asp Ala Leu Asp Pro Ala Tyr Ala Pro Gly Thr
            275                 280                 285

Gly Thr Pro Glu Ile Ala Gly Leu Thr Pro Ser Gln Ala Leu Glu Ile
            290                 295                 300

Ile Arg Gly Cys Gln Gly Leu Asn Val Met Gly Cys Asp Leu Val Glu
305                 310                 315                 320

Val Ser Pro Pro Tyr Asp Leu Ser Gly Asn Thr Ala Leu Leu Ala Ala
                325                 330                 335

Asn Leu Leu Phe Glu Met Leu Cys Ala Leu Pro Lys Val Thr Thr Val
            340                 345                 350

<210> SEQ ID NO 2
<211> LENGTH: 1700
<212> TYPE: DNA
<213> ORGANISM: Homo sapiens
<220> FEATURE:
<221> NAME/KEY: CDS
<222> LOCATION: (136)...(1194)

<400> SEQUENCE: 2
tactataggg agtcgaccca cgcgtccgcg ggttccggct ctggcgcgtg cacactcgcc      60
tcgccgttcg ggaccagcca gatcgcggcg gcctcgcggg cggtytggtc ggtgaggtct    120
tggccgcgcg cggca atg ctg agg ctg ctg gcg tcc ggg tgc gcc cgg ggc     171
                Met Leu Arg Leu Leu Ala Ser Gly Cys Ala Arg Gly
                  1               5                  10 ccg ggg ccc ggc gtg ggc gcg cgt cct gcc gca ggg ctc ttt cat ccg      219
Pro Gly Pro Gly Val Gly Ala Arg Pro Ala Ala Gly Leu Phe His Pro
            15                  20                  25 ggg cgc cgc cag agc cgc cag gct tcc gac gcg ccc cgg aac cag ccc      267
Gly Arg Arg Gln Ser Arg Gln Ala Ser Asp Ala Pro Arg Asn Gln Pro
        30                  35                  40 ccc agc ccc gag ttc gtg gcc cgg ccg gtg ggc gtc tgc tcc atg atg      315
Pro Ser Pro Glu Phe Val Ala Arg Pro Val Gly Val Cys Ser Met Met
45                  50                  55                  60
```

-continued

| | | | | | | | | | | | | | |
|---|---|---|---|---|---|---|---|---|---|---|---|---|---|
| cgc | ctg | ccg | gtg | cag | acc | tcc | ccc | gag | ggg | ctg | gac | gct | gcc ttc atc |
| Arg | Leu | Pro | Val | Gln | Thr | Ser | Pro | Glu | Gly | Leu | Asp | Ala | Ala Phe Ile |
| | | | | 65 | | | | 70 | | | | | 75 |

363

| | | | | | | | | | | | | |
|---|---|---|---|---|---|---|---|---|---|---|---|---|
| ggg | gtg | ccc | ctg | gat | act | ggg | acc | tcc | aac | cgg | cct | ggg gcg aga ttc |
| Gly | Val | Pro | Leu | Asp | Thr | Gly | Thr | Ser | Asn | Arg | Pro | Gly Ala Arg Phe |
| | | | 80 | | | | | 85 | | | | 90 |

411

| | | | | | | | | | | | | |
|---|---|---|---|---|---|---|---|---|---|---|---|---|
| gga | cct | cgc | cgc | atc | cgg | gaa | gaa | tca | gtg | atg | ctt | cgg aca gtc aat |
| Gly | Pro | Arg | Arg | Ile | Arg | Glu | Glu | Ser | Val | Met | Leu | Arg Thr Val Asn |
| | | 95 | | | | | 100 | | | | | 105 |

459

| | | | | | | | | | | | | |
|---|---|---|---|---|---|---|---|---|---|---|---|---|
| cct | agc | acg | ggg | gcc | ctc | ccc | ttc | cag | tcc | ctc | atg | gtt gca gac cta |
| Pro | Ser | Thr | Gly | Ala | Leu | Pro | Phe | Gln | Ser | Leu | Met | Val Ala Asp Leu |
| | 110 | | | | | 115 | | | | | 120 | |

507

| | | | | | | | | | | | | |
|---|---|---|---|---|---|---|---|---|---|---|---|---|
| ggc | gat | gtg | aat | gtc | aat | ctt | tac | aac | ctt | cag | gac | agc tgc cgg caa |
| Gly | Asp | Val | Asn | Val | Asn | Leu | Tyr | Asn | Leu | Gln | Asp | Ser Cys Arg Gln |
| 125 | | | | | 130 | | | | | 135 | | 140 |

555

| | | | | | | | | | | | | |
|---|---|---|---|---|---|---|---|---|---|---|---|---|
| att | caa | gag | gcc | tat | gag | aaa | att | gta | gca | gct | ggc | tgt att cct ctg |
| Ile | Gln | Glu | Ala | Tyr | Glu | Lys | Ile | Val | Ala | Ala | Gly | Cys Ile Pro Leu |
| | | | | 145 | | | | | 150 | | | 155 |

603

| | | | | | | | | | | | | |
|---|---|---|---|---|---|---|---|---|---|---|---|---|
| acc | ttg | ggt | gga | gat | cac | aca | atc | aca | tat | ccc | ata | ttg caa gcg atg |
| Thr | Leu | Gly | Gly | Asp | His | Thr | Ile | Thr | Tyr | Pro | Ile | Leu Gln Ala Met |
| | | | 160 | | | | | 165 | | | | 170 |

651

| | | | | | | | | | | | | |
|---|---|---|---|---|---|---|---|---|---|---|---|---|
| gca | aaa | aag | cat | ggc | cca | gtg | ggg | ctg | ctg | cac | gtg | gat gcg cac acg |
| Ala | Lys | Lys | His | Gly | Pro | Val | Gly | Leu | Leu | His | Val | Asp Ala His Thr |
| | 175 | | | | | 180 | | | | | 185 | |

699

| | | | | | | | | | | | | |
|---|---|---|---|---|---|---|---|---|---|---|---|---|
| gac | acg | acc | gac | aag | gcc | cta | gga | gag | aag | ctc | tac | cac ggg gcg ccc |
| Asp | Thr | Thr | Asp | Lys | Ala | Leu | Gly | Glu | Lys | Leu | Tyr | His Gly Ala Pro |
| | 190 | | | | | 195 | | | | | 200 | |

747

| | | | | | | | | | | | | |
|---|---|---|---|---|---|---|---|---|---|---|---|---|
| ttc | cgc | cgg | tgt | gtg | gat | gag | ggt | ctc | ctg | gac | tgt | aag cgt gtg gtg |
| Phe | Arg | Arg | Cys | Val | Asp | Glu | Gly | Leu | Leu | Asp | Cys | Lys Arg Val Val |
| 205 | | | | | 210 | | | | | 215 | | 220 |

795

| | | | | | | | | | | | | |
|---|---|---|---|---|---|---|---|---|---|---|---|---|
| cag | att | ggc | atc | cgg | ggc | tct | tcc | acg | acc | ttg | gat | ccc tac aga tac |
| Gln | Ile | Gly | Ile | Arg | Gly | Ser | Ser | Thr | Thr | Leu | Asp | Pro Tyr Arg Tyr |
| | | | | 225 | | | | | 230 | | | 235 |

843

| | | | | | | | | | | | | |
|---|---|---|---|---|---|---|---|---|---|---|---|---|
| aac | cgg | agc | cag | ggc | ttc | cgg | gta | gtc | ctg | gct | gaa | gac tgc tgg atg |
| Asn | Arg | Ser | Gln | Gly | Phe | Arg | Val | Val | Leu | Ala | Glu | Asp Cys Trp Met |
| | | | 240 | | | | | 245 | | | | 250 |

891

| | | | | | | | | | | | | |
|---|---|---|---|---|---|---|---|---|---|---|---|---|
| aag | tcg | ctg | gtt | cct | ctg | atg | ggg | gaa | gtc | agg | cag | cag atg gga ggc |
| Lys | Ser | Leu | Val | Pro | Leu | Met | Gly | Glu | Val | Arg | Gln | Gln Met Gly Gly |
| | | | 255 | | | | | 260 | | | | 265 |

939

| | | | | | | | | | | | | |
|---|---|---|---|---|---|---|---|---|---|---|---|---|
| aaa | ccc | att | tat | atc | agc | ttt | gat | att | gac | gct | ctg | gat cct gcc tat |
| Lys | Pro | Ile | Tyr | Ile | Ser | Phe | Asp | Ile | Asp | Ala | Leu | Asp Pro Ala Tyr |
| 270 | | | | | 275 | | | | | 280 | | |

987

| | | | | | | | | | | | | |
|---|---|---|---|---|---|---|---|---|---|---|---|---|
| gcg | cca | ggg | aca | ggg | aca | cct | gaa | att | gct | ggt | ctc | act cct agt cag |
| Ala | Pro | Gly | Thr | Gly | Thr | Pro | Glu | Ile | Ala | Gly | Leu | Thr Pro Ser Gln |
| 285 | | | | | 290 | | | | | 295 | | 300 |

1035

| | | | | | | | | | | | | |
|---|---|---|---|---|---|---|---|---|---|---|---|---|
| gct | ctg | gag | atc | atc | agg | ggt | tgt | caa | ggc | ctg | aac | gtg atg ggc tgt |
| Ala | Leu | Glu | Ile | Ile | Arg | Gly | Cys | Gln | Gly | Leu | Asn | Val Met Gly Cys |
| | | | | 305 | | | | | 310 | | | 315 |

1083

| | | | | | | | | | | | | |
|---|---|---|---|---|---|---|---|---|---|---|---|---|
| gat | ctt | gtc | gaa | gtt | tca | cca | ccg | tat | gat | ctt | tct | ggg aac aca gcc |
| Asp | Leu | Val | Glu | Val | Ser | Pro | Pro | Tyr | Asp | Leu | Ser | Gly Asn Thr Ala |
| | | | 320 | | | | | 325 | | | | 330 |

1131

| | | | | | | | | | | | | |
|---|---|---|---|---|---|---|---|---|---|---|---|---|
| ctg | ctg | gcg | gct | aac | ctg | ctg | ttt | gag | atg | cta | tgt | gct ctc ccc aaa |
| Leu | Leu | Ala | Ala | Asn | Leu | Leu | Phe | Glu | Met | Leu | Cys | Ala Leu Pro Lys |
| | | 335 | | | | | 340 | | | | | 345 |

1179

| | | | | |
|---|---|---|---|---|
| gtg | aca | acc | gtc | tga gtcttgtgct cttcaagaca aaacagattg cgtcgctgac |
| Val | Thr | Thr | Val | * |
| | 350 | | | |

1234 aagttctcaa gaagaactta tgagtaagca gtctgagaac taaagagttt atgccaagaa  1294 aactttctgc tgaaagtgtc attgctggct gtgaagtcgg gataatcagt agaattctca  1354

```
                                                  -continued
cccaaacagc aacatttcta aggaacttgg attaattggg ggaaaaaaaa aggagtactt   1414
gtactgcttt gatttttttt cctttgatga aagatggagg ataaagggga agtgaggaga   1474
atttctttca agattatcta aacattagaa acatgacatt taaaaaaact atgaaataat   1534
actgtataag cattccatct caaaaaaaaa aaaaaaaaaa atacagcttc tcctatgagg   1594
tgcttagggc tgcatcttgg ttttaggacc cctgtgaacg taagtaaaaa gtataaagta   1654
acacggagag cctgggtgac agagtgagac tccgtctcca aaaaaa                 1700
```